United States Patent
Laporta Alcantara et al.

(10) Patent No.: US 10,413,501 B2
(45) Date of Patent: Sep. 17, 2019

(54) COSMETIC COMPOSITION CONTAINING HALOMONAS FERMENT EXTRACT, AND USE THEREOF

(71) Applicant: LUBRIZOL ADVANCED MATERIALS, INC., Cleveland, OH (US)

(72) Inventors: Olga Laporta Alcantara, Barcelona (ES); Nuria Alminana Domenech, Barcelona (ES); Albert Soley Astals, Barcelona (ES); Antonio Ferrer Montiel, Alicante (ES); Nuria Garcia Sanz, Alicante (ES)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 15/521,774

(22) PCT Filed: Oct. 28, 2015

(86) PCT No.: PCT/IB2015/058316
§ 371 (c)(1),
(2) Date: Apr. 25, 2017

(87) PCT Pub. No.: WO2016/067218
PCT Pub. Date: May 6, 2016

(65) Prior Publication Data
US 2017/0224602 A1    Aug. 10, 2017

(30) Foreign Application Priority Data
Oct. 28, 2014    (EP) .................................... 14382422

(51) Int. Cl.
| | |
|---|---|
| *A61K 8/02* | (2006.01) |
| *A61K 8/73* | (2006.01) |
| *A61Q 3/00* | (2006.01) |
| *A61Q 5/00* | (2006.01) |
| *A61Q 11/00* | (2006.01) |
| *A61Q 19/00* | (2006.01) |
| *A61K 8/99* | (2017.01) |
| *A61K 8/60* | (2006.01) |

(52) U.S. Cl.
CPC .................. *A61K 8/73* (2013.01); *A61K 8/60* (2013.01); *A61K 8/99* (2013.01); *A61Q 3/00* (2013.01); *A61Q 5/00* (2013.01); *A61Q 11/00* (2013.01); *A61Q 19/00* (2013.01); *A61K 2800/74* (2013.01); *A61K 2800/85* (2013.01)

(58) Field of Classification Search
None
See application file for complete search history.

(56) References Cited

PUBLICATIONS

Oren. Environmental Technology. 2010; 31(8-9): 825-837.*
Bejar et al. J Biotech. 1998; 61: 135-141. (Year: 1998).*
Martinez-Checa et al. Appl Microbiol Biotech. 2002; 58: 358-363. (Year: 2002).*
Scott, et al., "Connexins in epidermal homeostasis and skin disease", Biochim. Biophys. Acta., Aug; vol. 1818 (8), pp. 1952-1961 (2012).
Dbouk, et al., "Connexins: a myriad of functions extending beyond assembly of gap junction channels", Cell Communication and Signaling, vol. 7:4, pp. (2009).
Scott, et al., "Key functions for gap junctions in skin and hearing", Biochem J., 2011, vol. 438 (2), pp. 245-254 (2011).
Meşe et al., "Gap Junctions: Basic Structure and Function", J. Investig. Dermatol., vol. 127, pp. 2516-2524 (2007).
Dumont et al., "Two new lipoaminoacids with complementary modes of action: new prospects to fight out against skin aging." Intl. J. Cosmet. Science, vol. 32, pp. 9-27 (2010). (Abstract only).
Thornton, "Estrogens and aging skin", Dermatoendocrinol., 2013, vol. 5(2), pp. 264-270 (2013).
Wilkinson, et al., "Harry's Cosmeticology", Seventh edition, pp. Longman House, Essex, GB (1982).
Nelson, et al., "Application of microencapsulation in textiles", Int. J. Pharm., vol. 242(1-2), pp. 55-62 (2002).
Schaab, "Impregnating Fabrics with Microcapsules," HAPPI May pp. 84-86 (1986).
Hipler; "Biofunctional Textiles and the Skin" Curr. Probl. Dermatol. v.33, Int. J. Pharm., vol. 242(1-2), pp. 55-62 (2006).
Malcolm, et al., "Controlled release of a model antibacterial drug from a novel self lubricating silicone biomaterial",J. Cont. Release, vol. 97(2), pp. 313-320 (2004).
Gottschalck, et al., CTFA International Cosmetic Ingredient Dictionary & Handbook, 12th Edition pp. 3040-3065 (2008).
Kamerling et al., "Characterization by gas-liquid chromatography-mass spectrometry and proton-magnetic-resonance spectroscopy of pertrimethylsilyl methyl glycosides obtained in the methanolysis of glycoproteins and glycopeptides." *Biochemical Journal* 151.3 pp. 491-495 (1975).
Rojas Escudero et al., "Optimization of carbohydrate silylation for gas chromatography," Journal of Chromatography A, vol. 1027, pp. 117-120 (2004).
El-Fouly, et al., "Scrape-loading and dye transfer. A rapid and simple technique to study gap junctional intercellular communication," Exp. Cell Res., vol. 168(2), pp. 422-430 (1987).

(Continued)

*Primary Examiner* — David Browe
(74) *Attorney, Agent, or Firm* — Thoburn Dunlap; Fay Sharpe LLP

(57) ABSTRACT

A method of treatment and/or care of the skin includes administering a composition which includes a cosmetically or dermopharmaceutically effective quantity (between 0.000001% by weight and 5% by weight of the composition) of an exopolysaccharide produced by a strain of *Halomonas eurihalina*, or a ferment extract comprising the exopolysaccharide. The exopolysaccharide has a composition by weight of 0.5% to 45% of rhamnose, 0.1% to 25% of galactose, 0.5% to 30% of mannose, 50% to 95% for the sum of glucose and D-glucosamine, 0% to 10% of fucose and 0% to 12% of glucuronic acid, with the condition that the sum of the percentages does not exceed 100%.

12 Claims, No Drawings

(56) References Cited

PUBLICATIONS

Werner et al. "Keratinocyte-fibroblast interactions in wound healing," J Invest Dermatol., vol. 127(5), pp. 998-1008 (2007).
Oren, "Industrial and environmental applications of halophilic microorganism," Environmental Technology, vol. 31, No. 8-9, pp. 825-834 (2010).
Béjar, "Characterization of exopolysaccharides produced by 19 halophilic strains of the species," *Halomonas eurihalina*, Journal of biotechnology, vol. 61(2), pp. 135-141(1998).
Martínez-Checa, et al. "Characteristics of bioemulsifier V2-7 synthesized in culture media added of hydrocarbons: chemical composition, emulsifying activity and rheological properties." Bioresource Technology vol. 98.16, pp. 3130-3135 (2007).
Llamas, et al. "Halomonas maura is a physiologically versatile bacterium of both ecological and biotechnological interest." Antonie Van Leeuwenhoek 89.3 pp. 395-403 (2006).
Martinez-Canovas, et al. "A taxonomic study to establish the relationship between exopolysaccharide-producing bacterial strains living in diverse hypersaline habitats." Current Microbiology, vol. 48.5, pp. 348-353 (2004).

* cited by examiner ly to confer different properties for GJIC in skin. Keratinocytes express temporally and spatially as many as 10 different connexins depending on their degree of differentiation. Not all connexins form compatible hemichannels which allow GJIC. The ability of connexins to form heteromeric hemichannels seems to be restricted to members of the same phylogenetic subgroup. Compatibility and incompatibility of connexins also increases the spectrum of intercellular communication, since it allows the generation of separate communication compartments for different molecules [Scott C A and Kelsell D P, "*Key functions for gap junctions in skin and hearing*", Biochem J., 2011, Sep. 1; 438 (2): 245-54]. Hemichannels are carried to the cell surface via vesicles transported through microtubules and finally, the hemichannels fuse to the plasma membrane to form gap junctions [Meş e G et al., "*Gap Junctions: Basic Structure and Function*", J. Investig. Dermatol., 2007, 127, 2516-2524]. The level of GJIC of a cell might be dynamically regulated at all levels of synthesis, assembly and degradation of connexins but also seems to depend on the function of other cell adhesion molecules, tight junction components and cytoskeletal elements [Dbouk H A et al., "*Connexins: a myriad of functions extending beyond assembly of gap junction channels*", Cell Communication and Signaling, 2009, 7:4].

COSMETIC COMPOSITION CONTAINING HALOMONAS FERMENT EXTRACT, AND USE THEREOF

This application is the U.S. national phase and claims the priority of PCT Appln. No. PCT/IB2015/058316 filed Oct. 28, 2015 which claims priority to European application no. 14382422.5 filed Oct. 28, 2014 the disclosures of which are incorporated in their entireties by reference herein.

FIELD OF THE INVENTION

The disclosed technology relates to a ferment extract and an exopolysaccharide of bacterial origin for aging treatment. Said product is secreted by a strain of the *Halomonas eurihalina* species. This invention also relates to the use of said ferment extract or exopolysaccharide of bacterial origin in cosmetic or dermopharmaceutical compositions for the treatment and/or care of the skin, mucous membranes, hair and/or nails.

BACKGROUND OF THE INVENTION

The human epidermis is a multilayered, cohesive tissue with a unique functional architecture and it forms the primary barrier to the outside environment. Keratinocytes are the main component of the epidermis and their cohesion is essential in order to assure cell renewal and differentiation. The epidermal cells are linked one to another by special constructions named "junctions". Different types of junctions exist, with different roles, such as rigidity (anchoring junctions), water resistance (tight junctions) and cell communication (gap junctions). Gap junctions are clusters of intercellular channels that allow the exchange by diffusion of ions ($Ca^{2+}$, $Mg^{2+}$) and small metabolites (glucose), nutrients, and signaling molecules (cyclic adenosine monophosphate, cAMP, or cyclic guanosine monophosphate cGMP) of less than 1 kDa between adjacent cells. This direct cytoplasmic exchange of metabolites and ions is thought to coordinate the epidermal homeostasis. Gap Junction-mediated Intercellular Communication (GJIC) is important in different physiological processes including cell differentiation, proliferation and electrical transmission, and it contributes to intracellular signaling, too [Scott C A, et al., "*Connexins in epidermal homeostasis and skin disease*", Biochim. Biophys. Acta., 2012, August; 1818 (8): 1952-61]. This mechanism is strictly regulated and abnormal GJIC can result in several pathological disorders.

Gap junction channels consists of integral membrane proteins called connexins (Cx). Based on sequence similarities, connexins have been categorized into 2 phylogenetic groups, α and β, and they are named according to their molecular mass. The oligomerization of six connexin proteins forms a hemichannel, also named connexon. This connexon can be formed either from a single type of connexin (homomeric) or from more than one type (heteromeric). In addition, gap junctions may be homotypic, when two identical connexons assemble, or heterotypic, when two dissimilar connexons assemble between the two interacting cells [Dbouk H A et al., "*Connexins: a myriad of functions extending beyond assembly of gap junction channels*", Cell Communication and Signaling, 2009, 7:4]. Due to the number of potential combinations of the approximately twenty available connexins, gap junctions composed of different connexin types can have different properties, for example, different permeability to molecules and ions. Therefore, the expression of multiple connexin proteins in a cell type is Gap Junction-mediated Intercellular Communication (GJIC) is important in different physiological processes including cell differentiation, proliferation, electrical transmission and inflammation [Scott C A, et al., "*Connexins in epidermal homeostasis and skin disease*", Biochim. Biophys. Acta., 2012, August; 1818 (8): 1952-61]. The expression of some connexins, like Cx26 and Cx30, is upregulated during the initial response to wound healing, and Cx26 is upregulated in human hyperproliferative psoriatic lesions. Therefore, the upregulation of connexins, and particularly Cx26 and/or Cx30, might be a strategy for the treatment of skin inflammatory diseases and/or wound healing.

The decrease on cell communication is one of the mechanisms resulting in skin aging, i.e. the age-induced down-regulation of connexins is related with alterations in gap junctions [Dumont S et al., "*Two new lipoaminoacids*" Intl. J. Cosmet. Science, 2010, 32, 9-27]. The signs of decreased cellular communication are revealed on the skin's surface as fine lines, wrinkles, surface roughness, loss of elasticity, uneven skin tone, loss of firmness, or dryness. This age-related deterioration of the skin by down-regulation of connexins is particularly accelerated with the menopause. After menopause, many women suffer from a swift skin aging; skin becomes thinner with decreased collagen content, decreased elasticity, increased wrinkling and increased dryness. In postmenopausal women skin thickness decreases by 1.13% per postmenopausal year, with an associated decrease in collagen content (2% per post-menopausal year). The collagen content (types I and III) of skin is thought to decrease by as much as 30% in the first five years following the menopause [Thornton M J, "*Estrogens and aging skin*", Dermatoendocrinol., 2013, 5(2):264-70]. Collagen is secreted mainly by fibroblasts with other extracellular matrix proteins that provide skin firmness and elasticity.

Therefore, an increase on the levels of connexin proteins would improve the cell communication and it would treat and delay the signs of skin aging such as wrinkles, irregular skin pigmentation, loss of elasticity, collagen, skin firmness, thickness and dryness.

Surprisingly, the applicant of this invention has found a ferment extract and an exopolysaccharide of bacterial origin that is an alternative to the previously mentioned problems.

SUMMARY OF THE INVENTION

The disclosed technology provides a solution for the problem of aging of skin by the use of the ferment extract or exopolysaccharide excreted by a strain of *Halomonas eurihalina* species.

In accordance with one aspect, a method of treatment and/or care of the skin, mucous membranes, hair and/or nails includes administering a cosmetically or dermopharmaceutically effective quantity of a ferment extract or an exopolysaccharide produced by a strain of *Halomonas eurihalina* species.

In accordance with another aspect, a method of treatment and/or care of the skin, mucous membranes, hair and/or nails includes administering a composition including cosmetically or dermopharmaceutically effective quantity of a ferment extract or an exopolysaccharide produced by a strain of *Halomonas eurihalina* species.

In accordance with one aspect, a composition for treatment and/or care of the skin, mucous membranes, hair and/or nails includes a cosmetically or dermopharmaceutically effective quantity of a ferment extract or an exopolysaccharide produced by a strain of *Halomonas eurihalina* species and at least one cosmetically acceptable excipient and/or ingredient.

DESCRIPTION OF THE INVENTION

This invention relates to a ferment extract or an exopolysaccharide excreted by a strain of *Halomonas eurihalina* species, to the ferment extract or the exopolysaccharide for its use in the therapeutic treatment of the skin and/or mucous membranes, to the use of the ferment extract or the exopolysaccharide for the cosmetic, non-therapeutic treatment and/or care of the skin, mucous membranes, hair and/or nails, and to cosmetic or dermopharmaceutical compositions which comprise the ferment extract or exopolysaccharide. Surprisingly, the inventors of this invention have found that the aforementioned ferment extract or exopolysaccharide treats or prevents the aging of the skin. In one embodiment, the increase in the level of connexins treats or prevents the aging of the skin.

Definitions

In order to facilitate the comprehension of this invention, the meanings of some terms and expressions as used in the context of the invention are included.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

In the context of this invention the terms "produced", "secreted" and "excreted" are used indistinctly.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

The term "treatment", as used in the context of this specification when it is not accompanied by the qualifications "cosmetic, non-therapeutic", means the administration of a compound according to the invention to alleviate or eliminate a disease or disorder or reduce or eliminate one or more symptoms associated with this disease or disorder. The term "treatment" also covers the ability to alleviate or eliminate the physiological consequences of the disease or disorder.

When the term "treatment" is accompanied by the qualifications "cosmetic, non-therapeutic" they refer to the application of the compound to the skin, mucous membranes, hair and/or nails, typically with the aim of improving the cosmetic qualities of the skin, mucous membranes, hair and/or nails such as and not restricted to, their level of hydration, elasticity, firmness, shine, tone or texture, among others. The term "care" in this invention refers to the maintenance of the qualities of the skin, mucous membranes, hair and/or nails. These qualities are subject to improvement and maintained through a cosmetic treatment and/or care of the skin, mucous membranes, hair and/or nails, both in healthy subjects as well as those which present diseases and/or disorders of the skin and/or mucous membranes, such as and not restricted to, ulcers and lesions on the skin, psoriasis, dermatitis, acne or rosacea, among others.

The term "prevention", as used in this invention, refers to the ability of a compound of the invention to prevent, delay or hinder the appearance or development of a disease, disorder, condition or change before its appearance.

In the context of this invention, the term "aging" refers to the changes experienced by the skin with age (chronoaging) or through exposure to the sun (photoaging) or to environmental agents such as tobacco smoke, extreme climatic conditions of cold, heat, or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as spots, reddening, bags under the eyes or the appearance of hyperpigmented areas such as age spots or freckles among others, anomalous differentiation, hyperkeratinization, elastosis, keratosis, orange-peel skin, loss of collagen structure and other histological changes of the stratum corneum, hypodermis, dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and presents the same physical characteristics as aging, such as and not restricted to, flaccidity, sagging, changes to the color or irregularities in the pigmentation, abnormal and/or excessive keratinization.

Therefore, a first aspect of the present invention relates to the ferment extract excreted by a strain of *Halomonas eurihalina* species for its use in the therapeutic treatment of the skin, mucous membranes and/or nails. In one embodiment, the ferment extract has a molecular weight of at least 10 kDa. In one embodiment, the ferment extract contains at least one exopolysaccharide. In one embodiment, the ferment extract of *Halomonas eurihalina* species has a molecular weight of at least 10 kDa and contains at least one exopolysaccharide.

A second aspect of this invention relates to an exopolysaccharide excreted by a strain of *Halomonas eurihalina* species for its use in the therapeutic treatment of the skin, mucous membranes and/or nails. In one embodiment, the exopolysaccharide has a molecular weight of at least 10 kDa.

In one embodiment, the therapeutic treatment of the skin, mucous membranes and/or nails refers to re-epithelialization and/or wound healing of the skin, mucous membranes and/or nails, to the treatment and/or prevention of inflammation of the skin and/or mucous membranes, or to the treatment and/or prevention or those conditions, disorders and/or diseases which are a result of the lack or decrease in hydration of the skin, mucous membranes and/or nails. In one embodiment, the therapeutic treatment of the skin, mucous membranes and/or nails refers to re-epithelialization and/or wound healing of the skin, mucous membranes and/or nails, to the treatment and/or prevention of inflammation of the skin and/or mucous membranes, or to the treatment and/or prevention or those conditions, disorders and/or diseases which are a result of the lack or decrease in hydration of the skin, mucous membranes and/or nails, and the ferment extract of *Halomonas eurihalina* species has a molecular weight of at least 10 kDa and it contains at least one exopolysaccharide, or the exopolysaccharide has a molecular weight of at least 10 kDa.

In one embodiment, the inflammation of the skin and/or mucous membranes is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, inflammation of the mucous membrane of the vagina, inflammation of the oral mucous membrane, gingivitis, periodontitis, rhinitis, allergic rhinitis, among others. In one embodiment, the increase in the level of connexins Cx26 and/or Cx30 treats and/or prevents inflammation of the skin and/or mucous membranes.

In one embodiment, the conditions, disorders and/or diseases which are a result of the lack or decrease in hydration of the skin, mucous membranes and/or nails are selected from the group formed by xerosis, hyperkeratosis, reactive hyperkeratosis, palmar and plantar hyperkeratosis, corns or calluses, actinic keratosis, non-actinic keratosis, atopic dermatitis, contact eczema, seborrheic dermatitis, cradle cap on babies, acne, rosacea, nevus, ichthyosis, psoriasis, parakeratosis, pityriasis, lichen planus, palmoplantar keratoderma, couperose, vaginal dryness.

In another aspect, the present invention relates to the use of the ferment extract excreted by a strain of *Halomonas eurihalina* species for the cosmetic, non-therapeutic treatment and/or care of the skin, mucous membranes, hair and/or nails. In one embodiment, the ferment extract has a molecular weight of at least 10 kDa. In one embodiment, the ferment extract contains at least one exopolysaccharide. In one embodiment, the ferment extract of *Halomonas eurihalina* species has a molecular weight of at least 10 kDa and contains at least one exopolysaccharide. In one embodiment, the cosmetic, non-therapeutic treatment and/or care of the skin, mucous membranes, hair and/or nails is a treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails. In one embodiment, the ferment extract of *Halomonas eurihalina* species has a molecular weight of at least 10 kDa, it contains at least one exopolysaccharide and the cosmetic, non-therapeutic treatment and/or care of the skin, mucous membranes, hair and/or nails is a treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails.

In another aspect, the present invention relates to the use of the exopolysaccharide excreted by a strain of *Halomonas eurihalina* species for the cosmetic, non-therapeutic treatment and/or care of the skin, mucous membranes, hair and/or nails. In one embodiment, the exopolysaccharide has a molecular weight of at least 10 kDa. In one embodiment, the cosmetic, non-therapeutic treatment and/or care of the skin, mucous membranes, hair and/or nails is a treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails. In one embodiment, the exopolysaccharide has a molecular weight of at least 10 kDa and the cosmetic, non-therapeutic treatment and/or care of the skin, mucous membranes, hair and/or nails is a treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails.

In another embodiment, the therapeutic treatment, the cosmetic, non-therapeutic treatment and/or care of the skin increases the levels of connexins in the skin. According to the present invention, the increase in the level of connexins in the skin is understood as the increase in the amount of at least one connexin in the skin keratinocytes. In one embodiment, the connexin is connexin 26, connexin 30, connexin 30.3, connexin 31, connexin 31.1, connexin 37, connexin 43, connexin 46, or connexin 58, also named as connexin 59. In one embodiment, the therapeutic treatment the cosmetic, non-therapeutic treatment and/or care of the skin increases the levels of connexins in the skin and the ferment extract of *Halomonas eurihalina* species has a molecular weight of at least 10 kDa, it contains at least one exopolysaccharide, or the exopolysaccharide has a molecular weight of at least 10 kDa.

In another embodiment, the treatment and/or care of the skin is carried out by topical or transdermal application.

In another embodiment, the strain of *Halomonas eurihalina* species is a strain of *Halomonas eurihalina* species with deposit number LMG P-28571. Said strain has been deposited on Oct. 10, 2014 at the Belgian Coordinated Collection of Microorganisms (BCCM)/Laboratorium voor Microbiologie-Bacteriëverzameling (LMG) (BCCM/LMG) (University Ghent, K. L. Ledeganckstraat 35, B-9000 Ghent, Belgium) as institution legally recognized for said purpose according to the Budapest Treaty on the International Recognition of the Deposit of Microorganisms on Apr. 28, 1977.

In one embodiment, the exopolysaccharide or the exopolysaccharide contained in the ferment extract excreted by the bacterial strain of *Halomonas eurihalina* species contains the monosaccharides rhamnose, galactose, glucose, mannose and D-glucosamine. Optionally, the exopolysaccharide also contains fucose and/or glucuronic acid. Typically, the strain of *Halomonas eurihalina* species is a strain of *Halomonas eurihalina* species with deposit number LMG P-28571. In one embodiment, the exopolysaccharide shows a composition by weight of 0.5% to 45% of rhamnose, 0.1% to 25% of galactose, 0.5% to 30% of mannose, 50% to 95% for the sum of glucose and D-glucosamine and 0% to 10% of fucose and 0% to 12% of glucuronic acid, with the condition that the sum of the percentages does not exceed 100%. In another embodiment, the exopolysaccharide shows a composition by weight of 1% to 35% of rhamnose, 0.5% to 20% of galactose, 1% to 25% of mannose, 55% to 90% for the sum of glucose and D-glucosamine and 0% to 5% of fucose and 0% to 6% of glucuronic acid, with the condition that the sum of the percentages does not exceed 100%. In another embodiment, the exopolysaccharide shows a composition by weight of 1.5% to 30% of rhamnose, 1% to 10% of galactose, 1.5% to 20% of mannose, 65% to 85% for the sum of glucose and D-glucosamine and 0% to 3% of fucose and 0% to 4% of glucuronic acid, with the condition that the sum of the percentages does not exceed 100%. In one embodiment, the ratio glucose:D-glucosamine is between 90:1 and 1:35, between 85:1 and 1:25, or between 75:1 and 1:15.

In another embodiment, the exopolysaccharide excreted by the bacterial strain of *Halomonas eurihalina* species has a retention time between 4 and 8.5 minutes, or between 5 and 8 minutes, at a chromatographic analysis High Performance Liquid Chromatography (HPLC), with a chromatographic column PL AQUAGEL-OH 8 μm AQUEOUS SEC COLUMNS and 0.1 M sodium acetate in water as eluent. In one embodiment, the exopolysaccharide of *Halomonas eurihalina* species has a molecular weight of at least 10 kDa, and the excreted exopolysaccharide has a retention time between 4 and 8.5 minutes, or between 5 and 8 minutes, at a chromatographic analysis High Performance Liquid Chromatography (HPLC), with a chromatographic column PL AQUAGEL-OH 8 μm AQUEOUS SEC COLUMNS and 0.1 M sodium acetate in water as eluent and flow rate 0.8 ml/min. Typically, the strain of *Halomonas eurihalina* species is a strain of *Halomonas eurihalina* species with deposit number LMG P-28571. PL AQUAGEL-OH 8 μm AQUEOUS SEC COLUMNS is a column for aqueous Size Exclusion Chromatography, with a packaging having the capacity to separate compounds depending on its MW, applied to neutral, anionic and cationic water-soluble polymers and with a particle size of 8 μm, a pore size of 50 Å and a length/Internal Diameter of 300 mm×7.5 mm.

In another embodiment, the ferment extract is obtained through fermentation of the strain of *Halomonas eurihalina* species in a suitable culture medium, conventionally stirred and aerated for synthesizing and secreting said product to the culture medium followed by the isolation and purification. Fermentation can be carried out in a medium stirred and aerated at a temperature between 15° C. and 40° C., typically at 32° C., the medium having a pH between 5.5 and 9, typically around 7.0, adjusting it if necessary during fermentation. The duration of the fermentation is between 12 to 120 hours, in one embodiment between 24 and 72 hours, in other embodiment, between 36 and 48 hours. Typically, the strain of *Halomonas eurihalina* species is a strain of *Halomonas eurihalina* species with deposit number LMG P-28571.

In one embodiment, the method of isolation and purification of the ferment extract is carried out by the methods known by the person skilled in the art such as, centrifugation, filtration, ultrafiltration and dialysis. In a first step, centrifugation and filtration steps are directed to separate the strain of the *Halomonas eurihalina* species from the supernatant where the ferment extract is found. In one embodiment, ultrafiltration and dialysis of the supernatant are carried out with a polyethersulfone membrane which retains molecules of a molecular weight greater than 10,000 Da and the ferment extract with molecular weight of at least 10 kDa is obtained. In other embodiment, the exopolysaccharide is purified from the supernatant by precipitation via addition of ethanol, acetone or isopropanol. In another embodiment, the ultrafiltration and dialysis of the supernatant with a polyethersulfone membrane which retains molecules of a molecular weight greater than 10,000 Da and the precipitation via addition of ethanol, acetone or isopropanol are carried out to obtain the exopolysaccharide with a molecular weight of at least 10 kDa. In one embodiment, the strain of *Halomonas eurihalina* species is a strain of *Halomonas eurihalina* species with deposit number LMG P-28571.

In another embodiment, in the fermentation of the strain of *Halomonas eurihalina* species a culture medium containing exogenous sugars, such as and not restricted to, galactose, glucose, mannose, amygdalin, cellobiose, maltose, starch, glycogen, lactose, mixtures thereof and/or extracts containing mixtures of these sugars can be used as a carbon source. In one embodiment, an exogenous supply of glucose of 2 to 40 g/L, or from 5 to 25 g/L is provided.

In another embodiment, the culture medium may comprise additional nitrogen or carbon sources such as yeasts extracts, malt extracts or peptones, with concentrations of each one of these components of 0.1 to 20 g/L, or from 0.5 to 10 g/L.

In another embodiment, mineral salts are also provided for the fermentation culture of the strain of *Halomonas eurihalina* species and they are selected from among salts which provide the ions $Na^+$, $K^+$, $NH_4^+$, $CA^{2+}$, $Mg^{2+}$, $PO_4^{3-}$, $SO_4^{2-}$, $Cl^-$, $CO_3^{2-}$, or trace elements such as Cu, Mn, Fe and Zn.

In another embodiment, the exopolysaccharide comprised in the ferment extract produced by the strain of the *Halomonas eurihalina* species contains a natural sulfatation, without mediating any chemical modification, of up to 7% of sulfates, or up to 5% of sulfates.

In another embodiment, the exopolysaccharide comprised in the ferment extract produced by the strain of the *Halomonas eurihalina* species contains a chemical modification known by the person skilled in the art such as phosphorylation, sulfonation, acylation with for example acetyl, pyruvoyl, propionyl, succinyl, lactoyl or 3-hydroxybutyl groups, esterification with for example glyceryl, formation of metallic complexes of the exopolysaccharide and/or chemical sulfatation greater than 7%.

Another aspect of this invention relates to a cosmetic or dermopharmaceutical composition characterized in that it comprises a cosmetically or dermopharmaceutically effective quantity of the ferment extract or of the exopolysaccharide produced by a strain of *Halomonas eurihalina* species and at least one cosmetically and/or dermopharmaceutically acceptable excipient and/or ingredient. In one embodiment, the ferment extract of *Halomonas eurihalina* species has a molecular weight of at least 10 kDa and it contains at least one exopolysaccharide, or the exopolysaccharide has a molecular weight of at least 10 kDa. Typically, the strain of *Halomonas eurihalina* species is a strain of *Halomonas eurihalina* species with deposit number LMG P-28571. Said compositions can be prepared by the conventional methods known by the persons skilled in the art ["*Harry's Cosmeticology*", Seventh edition, (1982), Wilkinson J. B., Moore R. J., ed. Longman House; Essex, GB].

The cosmetically or dermopharmaceutically effective quantity of the ferment extract or of the exopolysaccharide produced by a strain of *Halomonas eurihalina* species in the composition of the invention to be administered, as well as its dosage, will depend on numerous factors, including age, condition of the patient, the nature or severity of the condition, disorder or disease to be treated and/or cared for, the route and frequency of administration of the ferment extract or of the exopolysaccharide.

"Cosmetically or dermopharmaceutically effective quantity" is understood to be a non-toxic but sufficient quantity of the ferment extract or exopolysaccharide to provide the desired effect. In one embodiment, the ferment extract or the exopolysaccharide produced by a strain of *Halomonas eurihalina* species is used at cosmetic or dermopharmaceutic concentrations to achieve the desired effect; in one embodiment, with regard to the total weight of the composition, between 0.0000000001% (by weight) and 20% (by weight), between 0.00000001% (by weight) and 10% (by weight), between 0.000001% (by weight) and 5% (by weight) or between 0.0001% (by weight) and 5% (by weight).

In another embodiment, the ferment extract or the exopolysaccharide of the invention can also be incorporated into cosmetic and/or dermopharmaceutical delivery systems and/or sustained release systems. In one embodiment, the ferment extract of *Halomonas eurihalina* species has a molecular weight of at least 10 kDa and it contains at least one exopolysaccharide, or the exopolysaccharide has a molecular weight of at least 10 kDa.

The term "delivery systems" relates to a diluent, adjuvant, excipient, vehicle or additive with which the ferment extract or the exopolysaccharide of the invention is administered. These cosmetic or dermopharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the ferment extract or the exopolysaccharide of the invention can be administered.

The term "sustained release" is used in a conventional sense relating to a delivery system of a compound which provides the gradual release of this compound during a period of time and in one embodiment, although not necessarily, with relatively constant compound release levels over a period of time.

Examples of delivery or sustained release systems include, without limiting sense, liposomes, mixed liposomes, oleosomes, niosomes, ethosomes, milliparticles, microparticles, nanoparticles and solid lipid nanoparticles, nanostructured lipid supports, sponges, cyclodextrins, vesicles, micelles, mixed micelles of surfactants, surfactant-phospholipid mixed micelles, millispheres, microspheres and nanospheres, lipospheres, millicapsules, microcapsules and nanocapsules, as well as microemulsions and nanoemulsions, which can be added to achieve a greater penetration of the ferment extract and/or to improve the pharmacokinetic and pharmacodynamic properties of it. In one embodiment, the delivery or sustained release systems are liposomes, surfactant-phospholipid mixed micelles and microemulsions, and water-in-oil microemulsions with an internal reverse micelle structure and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part. In one embodiment, the sustained release system should release a relatively constant quantity of the ferment extract or the exopolysaccharide of the invention. The amount of ferment extract or exopolysaccharide contained in the sustained release system will depend, for example, on where the composition is to be administered, the kinetics and duration of the release of the ferment extract or exopolysaccharide of the invention, as well as the nature of the condition, disorder and/or disease to be treated and/or prevented.

The composition containing the ferment extract or exopolysaccharide of this invention can also be adsorbed on solid organic polymers or solid mineral supports, such as and not restricted to, talc, bentonite, silica, starch or maltodextrin among others.

The compositions containing the ferment extract or exopolysaccharide produced by a strain of *Halomonas eurihalina* species can also be incorporated into fabrics, non-woven fabrics or medical devices which are in direct contact with the skin, thus releasing the ferment extract or exopolysaccharide of the invention whether by biodegradation of the binding system to the fabric, non-woven fabric or medical device, or due to the friction between them and the body, due to body moisture, the skin's pH or body temperature. Furthermore, the ferment extract or exopolysaccharide of the invention can be incorporated into the fabrics and non-woven fabrics used in the manufacture of garments that are in direct contact with the body. In one embodiment, the fabrics, non-woven fabrics and medical devices containing the ferment extract or exopolysaccharide of the invention are used for the treatment and/or prevention of conditions, disorders and/or diseases which improve or are prevented by the increase of the levels of connexins in the skin.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) HAPPI May 1986; Nelson G., "*Application of microencapsulation in textiles*", (2002), Int. J. Pharm., 242(1-2), 55-62; "*Biofunctional Textiles and the Skin*" (2006) *Curr. Probl. Dermatol.* v.33, Hipler U. C. and Elsner P., eds. S. Karger AG, Basel, Switzerland; Malcolm R. K. et al., "*Controlled release of a model antibacterial drug from a novel self-lubricating silicone biomaterial*", (2004), *J. Cont. Release,* 97(2), 313-320]. In one embodiment, the fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or dermopharmaceutical compositions containing the ferment extract or exopolysaccharide of this invention can be used in different types of compositions of topical or transdermal application, optionally including cosmetically and/or dermopharmaceutically acceptable excipients necessary for formulating the desired administration form.

The compositions of topical or transdermal application can be produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, liquid crystals, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

The cosmetic or dermopharmaceutical compositions of the invention may include agents which increase the percutaneous absorption of the compounds of this invention, for example and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or dermopharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the ferment extract or exopolysaccharide of the invention. The application area will be determined by the nature of the condition, disorder and/or disease to be treated and/or prevented.

Among the cosmetically or dermopharmaceutically acceptable excipients and/or ingredients contained in the cosmetic or dermopharmaceutical compositions described in this invention are additional ingredients commonly used in cosmetic or dermopharmaceutical compositions such as and not restricted to, agents which inhibit neuronal exocytosis, anticholinergic agents, agents which inhibit muscular contraction, anti-aging agents, anti-wrinkle agents, humectants, substances that retain moisture, alpha hydroxy acids, beta hydroxy acids, moisturizers, agents stimulating the synthesis of dermal or epidermal macromolecules and/or capable of inhibiting or preventing their degradation, collagen synthesis-stimulating agents, elastin synthesis-stimulating agents, decorin synthesis-stimulating agents, laminin synthesis-stimulating agents, defensin synthesis-stimulating agents, chaperone synthesis-stimulating agents, cAMP synthesis-stimulating agents, agents that modulate AQP-3, agents that modulate aquaporin synthesis, proteins from the aquaporin family, hyaluronic acid synthesis-stimulating agents, glycosaminoglycan synthesis-stimulating agents, fibronectin synthesis-stimulating agents, sirtuin synthesis-stimulating agents, heat shock proteins, heat shock protein synthesis-stimulating agents, agents that reduces the amount of nocturnin, agents inhibiting the nocturnin expression, lipolytic agents or agents stimulating lipolysis, venotonic agents, agents modulating PGC-1α expression, agents inhibiting the activity of PPARγ, agents which reduce the triglyceride content of adipocytes, anti-cellulite agents, agents delaying adipocyte differentiation, agents which diminish the sebum production, anti-seborrheic agents, mattifying agents, anti-acne agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of components of the stratum corneum, ceramides, fatty acids, agents that inhibit collagen degradation, agents that inhibit matrix metalloproteinases, agents that inhibit elastin degradation, agents that inhibit serine proteases such as kallikreins, leukocyte elastase or cathepsin G, agents stimulating fibroblast proliferation, agents stimulating keratinocyte proliferation, agents stimulating melanocyte proliferation, agents stimulating keratinocyte differentiation, antihyperkeratosis agents, comedolytic agents, anti-psoriasis agents, DNA repair agents, DNA protecting agents, stem cell protecting agents, stabilizers, agents for the treatment and/or care of sensitive skin, firming agents, anti-stretch mark agents, astringent agents, agents which inhibit the activity of PAR-2, agents stimulating wound healing, coadjuvant wound healing agents, agents stimulating reepithelialization, coadjuvant reepithelialization agents, cytokine growth factors, agents acting on capillary circulation and/or microcirculation, agents stimulating angiogenesis, agents that inhibit vascular permeability, agents acting on cell metabolism, agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and with the ferment extract or exopolysaccharide produced by a strain of *Halomonas eurihalina* species. In one embodiment, the ferment extract of *Halomonas eurihalina* species has a molecular weight of at least 10 kDa and it contains at least one exopolysaccharide. Likewise, the nature of these additional ingredients should not unacceptably alter the benefits of the ferment extract or exopolysaccharide of this invention. The nature of these additional ingredients can be synthetic or natural, such as plant extracts, or come from a biotechnological process, or from a combination of a synthetic process and a biotechnological process. Additional examples can be found in *CTFA International Cosmetic Ingredient Dictionary & Handbook,* 12th Edition (2008). In the context of this invention, biotechnological process is understood to be any process to produce the active ingredient, or part of it, in an organism, or in part of it.

In one embodiment, the cosmetic and/or dermopharmaceutical composition of the invention contains:
- between 0.0000000001% (by weight) and 20% (by weight) of the ferment extract or exopolysaccharide excreted by a strain of *Halomonas eurihalina* species;
- between 0.1% (in weight) and 20% (in weight) of an humectant selected from the group of (INCI Names) Glycerin, Propylene Glycol, Butylene Glycol, Pentylene Glycol, Caprylyl Glycol, Lactic Acid, Urea, Sodium Hyaluronate;
- between 0.1% (in weight) and 20% (in weight) of an emollient or skin conditioning selected from the group of (INCI Names) Dimethicone, Glyceryl Stearate, Caprylic/Capric Triglyceride, Cetearyl Alcohol, Lecithin, C12-15 Alkyl Benzoate, Squalane, Lanolin, Behenyl Alcohol, Tocopheryl Acetate, Panthenol, Butyrospermum Parkii Butter, Retinyl Palmitate, Retinol;
- between 0.1% (in weight) and 20% (in weight) of a surfactant selected from the group of (INCI Names) Xanthan Gum, Sodium Laureth Sulfate, Stearic Acid, Polysorbate 20, Polysorbate 80, Stearyl Alcohol, Cetyl Alcohol, Steareth-2, Ceteareth-20, Cocamidopropyl Betaine.

In one embodiment, the anti-wrinkle and/or antiaging agent is selected, for example and not restricted to, from the group formed by the extracts or hydrolyzed extracts of *Vitis vinifera, Rosa canina, Curcuma longa, Theobroma cacao, Ginkgo biloba, Leontopodium alpinum* or *Dunaliella salina* among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage [INCI: teprenone], Resistem™ [INCI: Globularia Cordifolia Ferment], Beautifeye™ [INCI: Albizia Julibrissin Bark Extract, Darutoside™ ], Meiritage™ [INCI: Astragalus Membranaceus Root Extract, Atractylodes Macrocephala Root Extract, Bupleurum Falcatum Root Extract], Senestem™ [INCI: Plantago Lanceolata Leaf Extract], Venuceane™ [INCI: Thermus Thermophilus Ferment] or Dermaxyl® [INCI: Palmitoyl Oligopeptide] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum], Regu®-Scence [INCI: Asparagus Officinalis Stem Extract, Sodium Benzoate, Potassium Sorbate, Gluconolactone, Calcium Gluconate], Syn-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine] or Preregen® [INCI: Glycine soja (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9], Shadownyl™ [INCI: Algae Extract, Hexylene Glycol, Caprylyl Glycol, Xanthan Gum] or DN AGE™ LS [INCI: *Cassia alata* leaf Extract] marketed by Laboratoires Sérobiologiques/Cognis/BASF, Algisum C® [INCI: Methylsilanol Mannuronate], Exage™ [INCI: Imidazolylethyl Diaminopropanamide] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Serilesine® [INCI: Hexapeptide-10], Leuphasyl® [INCI: Pentapeptide-18], Inyline® [INCI: Acetyl Hexapeptide-30], Aldenine® [INCI: Hydrolyzed Wheat Protein, Hydrolyzed Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman® [INCI: Dimethylmethoxy Chromanol], Chromabright® [INCI: Dimethylmethoxy Chromanyl Palmitate], Antarcticine® [INCI: Pseudoalteromonas Ferment Extract], dGlyage® [INCI: Lysine HCl, Lecithin, Tripeptide-9 Citrulline], Vilastene™ [INCI: Lysine HCl, Lecithin, Tripeptide-10 Citrulline], Hyadisine® [INCI: Pseudoalteromonas Ferment Extract], Hyanify™ [INCI: Saccharide Isomerate], Diffuporine® [INCI: Acetyl Hexapeptide-37], Silusyne® [INCI: Soybean (Glycine Soja) Oil, Sorbitan Sesquioleate, Isohexadecane, Sodium Hyaluronate, Lauryldimonium Hydroxypropyl Hydrolyzed Soy Protein, Acetyl Hexapeptide-39], Adifyline® [INCI: Acetyl Hexapeptide-38], Uplevity™ [INCI: Acetyl Tetrapeptide-2], Juveleven™ [INCI: Acetyl Hexapeptide-51 Amide], Seacode™ [INCI: Pseudoalteromonas Ferment Extract], Nocturshape™ [INCI: Plankton Extract], Actigym™ [INCI: Plankton Extract], or Telangyn™ [INCI: Acetyl Tetrapeptide-40] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract], Peptide Q10 [INCI: Pentapeptide-34 Trifluoroacetate], Telosense [INCI: Hydrolyzed Yeast Protein, Hydrolyzed Soy Protein] or Quintescine™ IS [INCI: Dipeptide-4] marketed by Vincience/ISP/Ashland, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium/Unipex Innovations, EquiStat [INCI: *Pyrus malus* Fruit Extract, *Glycine soja* Seed Extract] or Juvenesce [INCI: Ethoxydiglycol and Caprylic Triglyceride, Retinol, Ursolic Acid, Phytonadione, Ilomastat] marketed by Coletica/Engelhard/BASF, Ameliox™ [INCI: Carnosine, Tocopherol, *Silybum marianum* Fruit Extract], PhytoCellTec™ Symphytum [INCI: Isomalt, Symphytum Officinale Root Cell Culture, Lecithin, Sodium Benzoate], Snow Algae Powder [INCI: Chlamydocapsa Extract, Maltodextrin, Lecithin], Dermcom™ [INCI: Acacia Senegal Gum, Crocus Chrysanthus Bulb Extract], Anagain™ [INCI: Pisum Sativum (Pea), Sprout Extract] or PhytoCellTec™ Malus Domestica [INCI: *Malus domestica* Fruit Cell Culture] marketed by Mibelle Biochemistry, Bioxilift™ [INCI: *Pimpinella anisum* Extract], Vitagenyl® [INCI: *Prunus Persica* (Peach) Leaf Extract] or SMS Anti-Wrinkle® [INCI: *Annona squamosa* Seed Extract] marketed by Silab, Symvital® AgeRepair [INCI: *Zingiber Officinale* (Ginger) Root Extract] marketed by Symrise, Citrustem™ [INCI: Xanthan Gum, Sodium Benzoate, Gluconolactone, Calcium Gluconate], Melavoid™ [INCI: *Boerhavia Diffusa* Root Extract], Darkout™ [INCI: Hypoxis Rooperi Rhizome Extract, Caesalpinia Spinosa Gum] or Linefill™ [INCI: Dimethyl Isosorbide, *Sesamum Indicum* (Sesame) Seed Extract] marketed by Provital, Adipofill'in™ [INCI: Ornithine, Phospholipids, Glycolipids], Elix-IR™ [INCI: Polygonum Aviculare Extract] or Progeline™ [INCI: Trifluoroacetyl Tripeptide-2] marketed by Lucas Meyer, Amiperfect™ [INCI: *Gaultheria Procumbens* (Wintergreen) Leaf Extract] or Repulpami™ ER [INCI: Adansonia Digitata Pulp Extract, *Hibiscus Sabdariffa* Flower Extract] marketed by Alban Muller, Celloxyl® [INCI: Uapaca Bojeri Leaf Extract] or Resistress® [INCI: Sophora Japonica Flower Extract] marketed by Solabia, Actiporine™ 8G [INCI: Jania Rubens Extract] or EPS Seafill [INCI: Plankton Extract] marketed by Codif, Novhyal® Biotech G [INCI: Disodium Acetyl Glucosamine Phosphate] or Rubixyl® [INCI: Hexapeptide-47] marketed by Induchem, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

In another embodiment, the firming and/or redensifying and/or restructuring agent is selected, for example and not restricted to, from the group formed by extracts of *Malpighia punicifolia, Cynara scolymus, Gossypium herbaceum, Aloe Barbadensis, Panicum miliaceum, Morus nigra, Sesamum indicum, Glycine soja, Triticum vulgare*, Pronalen® Refirming HSC [INCI: Triticum Vulgare, Silybum Marianum, Glycine Soy, Equisetum Arvense, Alchemilla Vulgaris, Medicago Sativa, Raphanus Sativus], Lipoout™ [INCI: Plankton Extract] or Polyplant® Refirming [INCI: Coneflower, Asiatic Centella, Fucus, Fenugreek] marketed by Provital, Lanablue® [INCI: Sorbitol, Algae Extract] marketed by Atrium Biotechnologies/Unipex Innovations, Pepha®-Nutrix [INCI: Natural Nutrition Factor] marketed by Pentapharm/DSM, plant extracts containing isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma/Croda, Dermosaccharides® HC [INCI: Glycerin, Water (Aqua), Glycosaminoglycans, Glycogen], Aglycal® [INCI: Mannitol, Cyclodextrin, Glycogen, Arctostaphylos Uva Ursi Leaf Extract], Cytokinol® LS [INCI: Hydrolyzed Casein, Hydrolyzed Yeast Protein, Lysine HCl] or Firmiderm® LS9120 [INCI: Terminalia Catappa Leaf Extract, *Sambucus Nigra* Flower Extract, PVP, Tannic Acid] marketed by Laboratoires Serobiologiques/Cognis/BASF, Liftline® [INCI: Hydrolyzed Wheat Protein], Raffermine® [INCI: Hydrolyzed Soy Flour] or Ridulisse C® [Hydrolyzed Soy Protein] marketed by Silab, Serilesine® [INCI: Hexapeptide-10], Decorinyl™ [INCI: Tripeptide-10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Silusyne™ [INCI: Soybean (Glycine Soja) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Ursolisome® [INCI: Lecithin, Ursolic Acid, Atelocollagen, Xanthan Gum, Sodium Chondroitin Sulfate], Eperuline™ [INCI: Maltodextrin, Eperua Falcata Bark Extract] or Collalift® [INCI: Hydrolyzed Malt Extract] marketed by Coletica/Engelhard/BASF, Syn®-Coll [INCI: Palmitoyl Tripeptide-5] marketed by Pentapharm/DSM, Hydriame® [INCI: Water (Aqua), Glycosaminoglycans, Sclerotium Gum] marketed by Atrium Biotechnologies/Unipex Innovations, Sphingokine® NP [INCI: Caprooyl Phytosphingosine] marketed by Evonik, Body³ Complex™ [INCI: Bentonite, *Butyrospermum Parkii* (Shea) Nut Extract, *Persea Gratissima* (Avocado) Fruit Extract] marketed by Lucas Meyer, ProSynergen™ DF [INCI: *Lactobacillus/Ulkenia Amoeboidea* Ferment Extract Filtrate] marketed by Lonza or IP2000™ [INCI: Dextran, Trifluoroacetyl Tripeptide-2] marketed by Institut Européen de Biologie Cellulaire/Unipex Innovations, among others.

In another embodiment, the agent stimulating the synthesis of dermal or epidermal macromolecules is selected, for example and not restricted to, from the group formed by collagen synthesis-stimulating agents, elastin synthesis-stimulating agents, decorin synthesis-stimulating agents, laminin synthesis-stimulating agents, chaperone synthesis-stimulating agents, sirtuin synthesis-stimulating agents, sirtuin activating agents, aquaporin synthesis-modulating agents, fibronectin synthesis-stimulating agent, agents that inhibit collagen degradation, agents that inhibit elastin degradation, agents that inhibit serine proteases such as kallikreins, leukocyte elastase or cathepsin G, agents stimulating fibroblast proliferation, and DNA repairing agents and/or DNA protecting agents, such as and not restricted to extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of soy, malt, flax, sage, red clover, kakkon, white lupin plants, hazelnut extract, maize extract, yeast extract, beech shoot extracts, leguminous seed extract, plant hormone extract such as gibberellins, auxins or cytokinins, among others, or extract of zooplankton Salina, the fermentation product of milk with *Lactobacillus Bulgaricus*, asiaticosides and their derivatives, vitamin C and its derivatives, cinnamic acid and its derivatives, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma/Croda, Antarcticine® [INCI: Pseudoalteromonas Ferment Extract], Decorinyl® [INCI: Tripeptide-10 Citrulline], Serilesine® [INCI: Hexapeptide-10], Lipeptide [INCI: Hydrolyzed Vegetable Protein], Aldenine® [INCI: Hydrolyzed Wheat Protein, Hydrolyzed Soy Protein, Tripeptide-1], Relistase™ [INCI: Acetylarginyltriptophyl Diphenylglycine], Thermostressine™ [INCI: Acetyl Tetrapeptide-22], Peptide AC29 [INCI: Acetyl Tripeptide-30 Citrulline], Diffuporine™ [INCI: Acetyl Hexapeptide-37], Silusyne™ [INCI: Soybean (Glycine Soja) Oil, Sorbitan Sesquioleate, Isohexadecane, Sodium Hyaluronate, Lauryldimonium Hydroxypropyl Hydrolyzed Soy Protein, Acetyl Hexapeptide-39] or Adifyline™ [INCI: Acetyl Hexapeptide-38] marketed by Lipotec/Lubrizol, Drieline® PF [INCI:Yeast Betaglucan] marketed by Alban Muller, Phytovityl C® [INCI: Aqua, Zea Mays Extract] marketed by Solabia, Collalift® [INCI: Hydrolyzed Malt Extract] marketed by Coletica/Engelhard/BASF, Phytocohesine PSP™ [INCI: Sodium Beta-Sitosterol Sulfate] marketed by Vincience/ISP/Ashland, minerals such as calcium, among others, retinoids and their derivatives, isoflavonoids, carotenoids, lycopene, pseudodipeptides, retinoids and their derivatives such as retinol or retinyl palmitate, among others, or heparinoids, among others.

In another embodiment, the agent stimulating wound healing, the coadjuvant wound healing agent, the agent stimulating reepithelization and/or the coadjuvant reepithelialization agent is selected, for example and not restricted to, from the group formed by extracts of *Aristolochia clematis, Centella asiatica, Rosa moschata, Echinacea angustifolia, Symphytum officinale, Equisetum arvense, Hypericum perforatum, Mimosa tenuiflora, Persea gratissima, Prunus africanum, Tormentilla erecta, Aloe vera*, Polyplant® Epithelizing [INCI: *Calendula Officinalis, Hypericum Perforatum, Chamomilla Recutita, Rosmarinus Officinalis*] marketed by Provital, Cytokinol® LS 9028 [INCI: Hydrolyzed Casein, Hydrolyzed Yeast Protein, Lysine HCI] marketed by Laboratories Serobiologiques/Cognis or Deliner® [INCI: Zea May (Corn) Kernel Extract] marketed by Coletica/Engelhard/BASF, allantoin, cadherins, integrins, selectins, hyaluronic acid receptors, immunoglobulins, fibroblast growth factors, connective tissue growth factors, platelet-derived growth factors, vascular endothelial growth factors, epidermal growth factors, insulin-like growth factors, keratinocyte growth factor, colony-stimulating factor, transforming growth factor beta, tumor necrosis factor-alpha, interferons, interleukins, matrix metalloproteinases, receptor protein tyrosine phosphatases, Antarcticine® [INCI: Pseudoalteromonas Ferment Extract], Decorinyl® [INCI: Tripeptide-10 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Bodyfensine™ [INCI: Acetyl Dipeptide-3 Aminohexanoate], Delisens™ [INCI: Acetyl Hexapeptide-49] or Diffuporine® [INCI: Acetyl Hexapeptide-37] marketed by Lipotec/Lubrizol, among others.

Applications

In another aspect, this invention refers to the use of the ferment extract produced by a strain of *Halomonas eurihalina* species in the preparation of a cosmetic or dermopharmaceutical composition for the treatment and/or care of the skin, mucous membranes, hair and/or nails. In one embodiment, the ferment extract has a molecular weight of at least 10 kDa. In one embodiment, the ferment extract contains at least one exopolysaccharide. In one embodiment, the ferment extract of *Halomonas eurihalina* species has a molecular weight of at least 10 kDa and it contains at least one exopolysaccharide. In one embodiment, the strain of *Halomonas eurihalina* species is a strain of *Halomonas eurihalina* species with deposit number LMG P-28571.

In another aspect, this invention refers to the use of the exopolysaccharide produced by a strain of *Halomonas eurihalina* species in the preparation of a cosmetic or dermopharmaceutical composition for the treatment and/or care of the skin, mucous membranes, hair and/or nails. In one embodiment, the exopolysaccharide has a molecular weight of at least 10 kDa. In one embodiment, the strain of *Halomonas eurihalina* species is a strain of *Halomonas eurihalina* species with deposit number LMG P-28571.

In one embodiment, the treatment and/or care of the skin, mucous membranes, hair and/or nails refers to treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails, re-epithelialization and/or wound healing of the skin, mucous membranes and/or nails, treatment and/or prevention of inflammation of the skin and/or mucous membranes, or treatment and/or prevention or those conditions, disorders and/or diseases which are a result of the lack or decrease in hydration of the skin, mucous membranes and/or nails. In one embodiment, the treatment and/or care of the skin, mucous membranes, hair and/or nails refers to treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails, re-epithelialization and/or wound healing of the skin, mucous membranes and/or nails, treatment and/or prevention of inflammation of the skin and/or mucous membranes, or treatment and/or prevention or those conditions, disorders and/or diseases which are a result of the lack or decrease in hydration of the skin, mucous membranes and/or nails, and the ferment extract of *Halomonas eurihalina* species has a molecular weight of at least 10 kDa and it contains at least one exopolysaccharide or the exopolysaccharide has a molecular weight of at least 10 kDa. In one embodiment, the strain of *Halomonas eurihalina* species is a strain of *Halomonas eurihalina* species with deposit number LMG P-28571.

In one embodiment, the inflammation of the skin and/or mucous membranes is selected, for example and not restricted to, from the group formed by psoriasis, sensitive skin, dermatitis, atopic dermatitis, contact dermatitis, diaper dermatitis, seborrheic dermatitis, eczema, rosacea, acne, hyperproliferative skin disease, burns, sunburn, paronychia, skin inflammation after surgery, after treatment with intense pulsed light therapy (IPL), after treatment with monochromatic pulsed light therapy (laser), after treatment with chemical peeling agents or after overexposure to aggressive external agents, inflammation of the mucous membrane of the vagina, inflammation of the oral mucous membrane, gingivitis, periodontitis, rhinitis, allergic rhinitis, among others. In one embodiment, the increase in the level of connexins Cx26 and/or Cx30 treats and/or prevents inflammation of the skin and/or mucous membranes.

In one embodiment, the conditions, disorders and/or diseases which are a result of the lack or decrease in hydration of the skin, mucous membranes and/or nails are selected from the group formed by xerosis, hyperkeratosis, reactive hyperkeratosis, palmar and plantar hyperkeratosis, corns or calluses, actinic keratosis, non-actinic keratosis, atopic dermatitis, contact eczema, seborrheic dermatitis, cradle cap on babies, acne, rosacea, nevus, ichthyosis, psoriasis, parakeratosis, pityriasis, lichen planus, palmoplantar keratoderma, couperose, vaginal dryness.

In another aspect, this invention refers to the use of the ferment extract produced by a strain of *Halomonas eurihalina* species in the preparation of a cosmetic or dermopharmaceutical composition for treatment and/or care of the skin which increases the levels of connexins in the skin. According to the present invention, the increase in the level of connexins in the skin is understood as the increase in the amount of at least one connexin in the skin keratinocytes. In one embodiment, the connexin is connexin 26, connexin 30, connexin 30.3, connexin 31, connexin 31.1, connexin 37, connexin 43, connexin 46, or connexin 58, also named as connexin 59. In one embodiment, the ferment extract of *Halomonas eurihalina* species has a molecular weight of at least 10 kDa, it contains at least one exopolysaccharide and the treatment and/or care of the skin increases the levels of connexins in the skin.

In another aspect, this invention refers to the use of the exopolysaccharide produced by a strain of *Halomonas eurihalina* species in the preparation of a cosmetic or dermopharmaceutical composition for treatment and/or care of the skin which increases the levels of connexins in the skin. According to the present invention, the increase in the level of connexins in the skin is understood as the increase in the amount of at least one connexin in the skin keratinocytes. In one embodiment, the connexin is connexin 26, connexin 30, connexin 30.3, connexin 31, connexin 31.1, connexin 37, connexin 43, connexin 46, or connexin 58, also named as connexin 59. In one embodiment, the exopolysaccharide of *Halomonas eurihalina* species has a molecular weight of at least 10 kDa, and the treatment and/or care of the skin increases the levels of connexins in the skin.

An additional aspect of this invention refers to a method of treatment and/or care of the skin, mucous membranes, hair and/or nails which comprises the administration of a cosmetically or dermopharmaceutically effective quantity of the ferment extract produced by a strain of *Halomonas eurihalina* species. In one embodiment, the ferment extract has a molecular weight of at least 10 kDa. In one embodiment, the ferment extract contains at least one exopolysaccharide. In one embodiment, the ferment extract of *Halomonas eurihalina* species has a molecular weight of at least 10 kDa and it contains at least one exopolysaccharide. In one embodiment, the strain of *Halomonas eurihalina* species is a strain of *Halomonas eurihalina* species with deposit number LMG P-28571.

An additional aspect of this invention refers to a method of treatment and/or care of the skin, mucous membranes, hair and/or nails which comprises the administration of a cosmetically or dermopharmaceutically effective quantity of the exopolysaccharide produced by a strain of *Halomonas eurihalina* species. In one embodiment, the exopolysaccharide has a molecular weight of at least 10 kDa. In one embodiment, the strain of *Halomonas eurihalina* species is a strain of *Halomonas eurihalina* species with deposit number LMG P-28571

In one embodiment, the method of treatment and/or care of the skin, mucous membranes, hair and/or nails refers to a method of treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails, re-epithelialization and/or wound healing of the skin, mucous membranes and/or nails, treatment and/or prevention of inflammation of the skin and/or mucous membranes, or treatment and/or prevention or those conditions, disorders and/or diseases which are a result of the lack or decrease in hydration of the skin, mucous membranes and/or nails. In one embodiment, the method of treatment and/or care of the skin, mucous membranes, hair and/or nails refers to a method of treatment of stimulation of collagen synthesis, treatment and/or prevention of skin aging, treatment and/or prevention of skin wrinkles, treatment for improving skin firmness and/or for the prevention of loss of skin firmness, treatment and/or prevention of dry skin, chapped lips, dandruff, dry hair, brittle hair and/or nails, re-epithelialization and/or wound healing of the skin, mucous membranes and/or nails, treatment and/or prevention of inflammation of the skin and/or mucous membranes, or treatment and/or prevention or those conditions, disorders and/or diseases which are a result of the lack or decrease in hydration of the skin, mucous membranes and/or nails, and the ferment extract of *Halomonas eurihalina* species has a molecular weight of at least 10 kDa and it contains at least one exopolysaccharide, or the exopolysaccharide of *Halomonas eurihalina* species has a molecular weight of at least 10 kDa. In one embodiment, the strain of *Halomonas eurihalina* species is a strain of *Halomonas eurihalina* species with deposit number LMG P-28571.

In one embodiment, the conditions, disorders and/or diseases which are a result of the lack or decrease in hydration of the skin, mucous membranes and/or nails are selected from the group formed by xerosis, hyperkeratosis, reactive hyperkeratosis, palmar and plantar hyperkeratosis, corns or calluses, actinic keratosis, non-actinic keratosis, atopic dermatitis, contact eczema, seborrheic dermatitis, cradle cap on babies, acne, rosacea, nevus, ichthyosis, psoriasis, parakeratosis, pityriasis, lichen planus, palmoplantar keratoderma, couperose, vaginal dryness.

In another aspect, this invention refers to a method of increase of the levels of connexins in the skin which comprises the administration of a cosmetically or pharmaceutically effective quantity of the ferment extract produced by a strain of *Halomonas eurihalina* species. In one embodiment, the ferment extract has a molecular weight of at least 10 kDa. In one embodiment, the ferment extract contains at least one exopolysaccharide. In one embodiment, the ferment extract of *Halomonas eurihalina* species has a molecular weight of at least 10 kDa and it contains at least one exopolysaccharide. In one embodiment, the strain of *Halomonas eurihalina* species is a strain of *Halomonas eurihalina* species with deposit number LMG P-28571.

In another aspect, this invention refers to a method of increase of the levels of connexins in the skin which comprises the administration of a cosmetically or pharmaceutically effective quantity of the exopolysaccharide produced by a strain of *Halomonas eurihalina* species. In one embodiment, the exopolysaccharide has a molecular weight of at least 10 kDa. In one embodiment, the strain of *Halomonas eurihalina* species is a strain of *Halomonas eurihalina* species with deposit number LMG P-28571.

In another aspect, the ferment extract or the exopolysaccharide produced by a strain of *Halomonas eurihalina* species can be administered by any means that causes its contact with the site of action in a mammal's body, typically that of a human being, and in the form of a composition which contains it. The administration of the ferment extract produced by a strain of *Halomonas eurihalina* species is carried out topically or transdermally. In one embodiment, topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of the application or administration can vary widely, depending on the needs of each subject, suggesting a range of application or administration from once per month to 10 times per day, from once per week to 4 times per day, from three times per week to three times per day, or once per day.

Deposit of Biological Material

The strain of the *Halomonas eurihalina* species was deposited at the Belgian Coordinated Collection of Microorganisms (BCCM)/Laboratorium voor Microbiologie-Bacteriëverzameling (LMG) (University Ghent, K. L. Ledeganckstraat 35, 9000 Ghent, Belgium) under the conditions of the Budapest Treaty. The deposit was done on Oct. 10, 2014 and the deposit number was LMG P-28571.

EXAMPLES

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as approximated, i.e., subject to a variability of ±5%, ±3%, ±1%, ±0.1%, or ±0.01% of the indicated value. It is to be understood that the upper and lower amount, range, and ratio limits set forth herein may be independently combined. Similarly, the ranges and amounts for each element of the technology described herein can be used together with ranges or amounts for any of the other elements.

Example 1: Obtaining the Exopolysaccharide Secreted by the Strain of *Halomonas eurihalina* Species with Deposit Number LMG P-28571

A) Culture Process of the Strain of the *Halomonas eurihalina* Species with Deposit Number LMG P-28571.

The strain of the *Halomonas eurihalina* species with deposit number LMG P-28571 is cultivated in a fermenter, at 32° C. and at a pH of 7.0, in a culture medium containing water, 10 g/L of glucose as source of carbon, 3 g/L of yeast extract and 3 g/L of malt extract and 5 g/L of pea peptone as sources of carbon and nitrogen, and a salt solution containing 9.8 g/L NaCl, 1.7 g/L magnesium chloride hexahydrate, 2.5 g/L magnesium sulfate heptahydrate, 0.25 g/L potassium chloride, 0.05 g/L calcium chloride dehydrate, 0.05 g/L sodium bicarbonate, sodium bromide and iron chloride trace salts. It is inoculated at a 520 nm absorbance of 0.2 Absorbance Units from a pre-culture in an exponential state of growth and the fermentation duration is extended to approximately 40 hours of culture. The culture is supplied with a sufficient air supply, and stirred at stirring speeds between 300 and 600 rpm.

B) Purification of the Exopolysaccharide of the Strain of the *Halomonas eurihalina* Species Deposited under Deposit Number LMG P-28571.

The bacteria is separated from the resulting fermentation broth described in example 1a) containing the exopolysaccharide by centrifugation at 18,000 g for 1 hour. The removal of the bacteria is completed by filtration at a final pore size of 0.20 μm. Subsequently, the filtered broth is dialyzed with a 10,000 Da cut membrane, the exopolysaccharide being retained by the membrane. Finishing of the purification is performed by freeze-drying of the dialyzed exopolysaccharide.

Example 2: Physicochemical Characterization of the Exopolysaccharide Excreted by the Strain of the *Halomonas eurihalina* Species with Deposit Number LMG P-28571

A high performance liquid chromatography (HPLC) and infrared spectroscopy (IR) analysis (refractive index detector) are performed for the physicochemical characterization of the exopolysaccharide produced by the strain of the *Halomonas eurihalina* species with deposit number LMG P-28571 and on the monosaccharide content of the exopolysaccharide obtained in accordance with example 1.

High Performance Liquid Chromatography (HPLC) and Infrared Spectroscopy (IR) Analysis In order to carry out the HPLC-IR chromatograms, samples are prepared from the exopolysaccharide obtained in accordance with example 1, diluting them in water at 2 mg/mL and filtering them with 0.2 μm polyethersulfone filters. The HPLC analysis is carried out using 100 μL injection of the sample on an LC20A SHIMADZU chromatography equipment. The chromatographic column used is a PL AQUAGEL-OH 8 μm AQUEOUS SEC COLUMNS, and the detector, RID-10A™ Refractive Index Detector (Shimadzu). The solvent used is 0.1 M sodium acetate in water and the flow rate is 0.8 ml/min. PL AQUAGEL-OH 8 μm AQUEOUS SEC COLUMNS is a column for aqueous Size Exclusion Chromatography, with a packaging having the capacity to separate compounds depending on its MW, applied to neutral, anionic and cationic water-soluble polymers and with a particle size of 8 μm, a pore size of 50 Å and a length/Internal Diameter of 300 mm×7.5 mm.

The result of the analysis shows a retention time between 5 and 8 minutes.

Analysis of Monosaccharides

In order to perform the monosaccharide analysis from the solid, the method described by Kamerling et al., *Biochem. J.*, 1975 151, 491-495 as later modified by Montreuil et al. in, *Glycoproteins. In Carbohydrate analysis: a practical approach*, 1986, Eds Chaplin & Kennedy, I.R.L Press, Oxford, Washington D.C., 143-204 is followed. The derivatization of the hydrolyzed monosaccharides is carried out according to literature methods [Rojas Escudero et al., *J. Chromatogr. A.*, 2004, 1027:117-120]. A ZEBRON® ZB-1701 (Phenomenex®) column, an injector temperature of 250° C., a detector temperature of 280° C., and oven temperature ramp programming of 160° C. to 250° C. are used for the chromatographic analysis.

The analysis of the exopolysaccharide obtained according to example 1, results in: 75% of glucose, 13% of mannose, 2% of rhamnose, 2% of D-glucosamine, and 7% of galactose, and 1% of fucose.

In a second repetition of the culture and preparation of the exopolysaccharide according to example 1, the percentages resulting from the analysis are: 52% of glucose, 10% of mannose, 12% of rhamnose, 20% of D-glucosamine, 6% of galactose, 1% of fucose, and 1% of glucuronic acid.

Example 3: Study of the Increase of Gap Junctions Intercellular Communication in Human Keratinocyte HaCaT Cell Line by the Scrape-Loading Dye Transfer Gap Junctions Intercellular Communication (GJIC) of the cells is assessed by the Scrape-Loading Dye Transfer (SLDT) technique described by el-Fouly M H, et al., ["*Scrape-loading and dye transfer. A rapid and simple technique to study gap junctional intercellular communication.*" *Exp. Cell Res.*, 1987 February; 168(2):422-30] with some modifications. The effect of the exopolysaccharide produced by the strain of *Halomonas eurihalina* species with deposit number LMG P-28571 obtained in accordance with example 1 on GJIC is studied in Human Keratinocyte HaCaT cell line.

HaCat cells (DKFZ) are seeded at $1.0 \times 10^5$ cells/well in 24-wells plates and incubated in culture medium (DMEM, high glucose, GlutaMAX™ Supplement, supplemented with 10% Fetal Bovine Serum) (Gibco®) at 37° C. and 5% $CO_2$ for 24 hours. Then, cells are treated for 24 hours with the exopolysaccharide produced by the strain of *Halomonas eurihalina* species with deposit number LMG P-28571 obtained in accordance with example 1 at 0.5 mg/ml in culture medium, and culture medium (DMEM, high glucose, GlutaMAX™ Supplement, supplemented with 10% Fetal Bovine Serum) (Gibco®) (as basal conditions) at 37° C. and 5% $CO_2$ for 24 h. All treatments are made with two wells per condition. At the end of the incubation period, the cells are rinsed twice with phosphate-buffer saline (PBS). The PBS is removed, and 400 µl of PBS containing Lucifer Yellow (LY) (Life Technologies) (0.5 mg/ml), a Gap Junctions permeable tracer, and Gap Junctions non-permeant compound Rhodamine Dextran (RhD) (Life Technologies) (0.5 mg/ml) are added to the wells. A scalpel is used to create one scrape line across the cell monolayer. Cells are incubated for 30 minutes in the dark at room temperature to allow dye transfer. Then, cells are rinsed 4 times with PBS and fixed for 30 minutes at room temperature with 4% (w/v) paraformaldehyde. The distance at which the fluorescent dye diffuses away from the scrape line during a certain period is indicative of GJIC level within a culture. Gap Junctional dye transfer is observed with a fluorescence microscope (Zeiss) using a 10× objective. The distance of Lucifer Yellow dye migration is measured from the cell layer at the scrape to the edge of the dye front that is visually detectable. Four independent assays in duplicate (2 wells per condition) are performed. The pictures taken are analyzed using the image analysis software (Zen lite 2010™ (blue edition), Zeiss). Table 1 shows the mean values of 4 independent experiments.

TABLE 1

| Product | Concentration | Fold-Induction of GJIC respect to basal conditions |
|---|---|---|
| Exopolysaccharide of example 1 | 0.5 mg/ml | 1.47 |

In the SLDT assay, the exopolysaccharide of the invention shows an increase in the distance at which the fluorescent dye diffuses respect to basal condition (Medium) demonstrating to be effective improving GJIC in HaCat cells.

Example 4: Study of the Modulation of RNA Expression in Human Epidermal Keratinocytes from Adult Using the Human Gap Junctions $RT^2$ PCR Array RT-PCR is a sensitive method for the detection of mRNA expression levels and may be a useful tool for the identification of specific gap junction's expression activating compounds. The potential and non-cytotoxic candidate is evaluated for the activation of gap junctions (GJs) expression and modulation of RNA expression using the Human Gap junctions Predesigned 96-well panel for use with SYBR® Green (BioRad) in Human Epidermal Keratinocytes, from adult (HEKa) (Cascade Biologics). This kit studies the expression profiles of 84 key genes encoding components, interactors, and regulators of Gap Junctions, plus three housekeeping genes, and five controls. The expression profile of Gap Junction components and regulators may lead to a better understanding of molecular mechanism behind Gap Junctions-mediated cell biology. Using real time PCR, it is analyzed the specific pattern of RNA profile induced by the exopolysaccharide produced by the strain of *Halomonas eurihalina* species with deposit number LMG P-28571 obtained in accordance with example 1, at 0.5 mg/ml compared to the basal levels of untreated cells (negative control) in HEKa.

HEKa cells are seeded at $5.0 \times 10^5$ cells/well in 6-well plates and incubated in Epilife® with defined Growth Supplement (EDGR) (Gibco) at 37° C. and 5% $CO_2$ for 24 hours. After 24 hours, the medium is removed and cells are incubated with 0.5 mg/ml of the exopolysaccharide produced by the strain of *Halomonas eurihalina* species with deposit number LMG P-28571 obtained in accordance with example 1, and as basal control two wells of HEKa cells are incubated with medium only (EpiLife® with defined Growth Supplement (EDGR) (Gibco). 24 hours after incubation, the cells are lysed directly in the wells, and RNA is extracted and purified from each replica and each condition by means of the RNeasy™ Plus Mini kit by Qiagen. The lysed cells are homogenized and the RNases are inactivated. The genomic DNA is removed from the samples by using gDNA Eliminator spin columns. Then, the samples are passed through special RNA binding columns and after several microcentrifugation washes to eliminate contaminants and impurities, the purified RNA is eluted with 50 µl of ultrapure water. After RNA elution, quantification and analysis of purity of RNA samples are performed with a biophotometer (Eppendorf). For each sample, 7.5 µg of high quality RNA is retrotranscribed with iScript advanced (Bio-Rad) in a final volume of 20 µl. Complete reaction mixture is incubated in a thermal cycler (Eppendorf) at 42° C. for 30 minutes, the reaction is stopped at 85° C. for 5 minutes. Complementary DNA is amplified by qPCR in a real-time PCR thermocycler (BioRad) using SYBR® green supermix (BioRad) in the Human Gap junctions Predesigned 96-well panel for use with SYBR® Green (BioRad). SYBR Green binds to double-stranded DNA molecules and emits fluorescence which is quantified, and the fluorescence intensity is proportional to the amount of the product in the PCR reaction. Cycling conditions in BioRad CFX96™ instrument are: 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression ($\Delta\Delta(Ct)$) method with default threshold values using CFX Manager Software (BioRad).

The results obtained for the exopolysaccharide according to example 1 are shown in the next tables.

TABLE 2

Connexin Genes regulated by the exopolysaccharide in accordance with example 1

| Protein Name | Gene Symbol | Gene Name | Fold induction |
|---|---|---|---|
| Cx43 | GJA1 | Gap junction alpha-1 protein | 2.05 |
| Cx46 | GJA3 | Gap junction alpha-3 protein | 3.30 |
| Cx37 | GJA4 | Gap junction alpha-4 protein | 2.69 |
| Cx58 | GJA9 | Gap junction alpha-9 protein | 2.45 |
| Cx26 | GJB2 | Gap junction beta-2 protein | 1.63 |
| Cx31 | GJB3 | Gap junction beta-3 protein | 1.14 |
| Cx30 | GJB6 | Gap junction beta-6 protein | 3.70 |

TABLE 3

Cell signaling Genes regulated by the exopolysaccharide in accordance with example 1

| Symbol | Gene Name | Fold induction |
|---|---|---|
| ADCY3 | Adenylate cyclase 3 | 1.49 |
| MAP3K2 | Mitogen-activated protein kinase kinase kinase 2 | 3.08 |
| MAPK3 | Mitogen-activated protein kinase 3 | 1.12 |
| MAPK7 | Mitogen-activated protein kinase 7 | 1.86 |
| PRKCB | protein kinase C, beta | 2.43 |
| PRKG1 | protein kinase, cGMP-dependent, type I | 1.20 |
| GRB2 | Growth factor receptor-bound protein 2 | 1.48 |

TABLE 4

Connexin interacting Protein Genes regulated by the exopolysaccharide in accordance with example 1

| Symbol | Gene Name | Fold induction |
|---|---|---|
| DNB1 | Drebrin | 2.05 |
| TJP1 | Tight junction protein 1 | 1.25 |

TABLE 5

Tubulin Genes regulated by the exopolysaccharide in accordance with example 1

| Symbol | Gene Name | Fold induction |
|---|---|---|
| TUBA1C | Tubulin, alpha 1c | 4.93 |
| TUBA4A | Tubulin, alpha 4a | 1.7 |

TABLE 6

Others Genes regulated by the exopolysaccharide in accordance with example 1

| Symbol | Gene Name | Fold induction |
|---|---|---|
| B2M | beta-2-microglobulin | 1.61 |
| GUSB | glucuronidase, beta | 1.34 |
| ITPR2 | inositol 1,4,5-trisphosphate receptor, type 2 | 1.35 |
| PANX1 | pannexin 1 | 1.29 |
| PANX2 | pannexin 2 | 2.15 |

The results obtained for the exopolysaccharide according to example 1 show that it increases the expression of genes involved in cell communication at different levels in HEKa, such as synthesis of connexins, transport of hemichannels to the membrane and assembly, turnover and modulation of gap junctions.

Example 5: Effect of the Exopolysaccharide Produced by the Strain of *Halomonas eurihalina* Species with Deposit Number LMG P-28571 on Epidermal-Dermal Cell-Cell Communication Aging depletes the communication process between cells. Crosstalk between fibroblasts and keratinocytes is essential for regeneration, repair and growth of the skin, and involves the activity of a number of messengers such as growth factors and cytokines. Keratinocytes are the primary source of growth factors, which may stimulate not only keratinocytes themselves but also fibroblasts through paracrine signaling and greatly affect the molecular constitution of the extracellular matrix (ECM) (Werner S, Krieg T, Smola H. *Keratinocyte-fibroblast interactions in wound healing. J Invest Dermatol.* 2007 May; 127(5):998-1008). In this study, the effect of the exopolysaccharide produced by the strain of *Halomonas eurihalina* species with deposit number LMG P-28571, obtained in accordance with example 1, on keratinocyte-fibroblast communication from a 54 year-old donor is evaluated and compared with the keratinocyte-fibroblast communication from a younger (39 year old) donor. The fibroblasts from the 54 year-old donor are incubated with supernatants of keratinocytes which are treated first with the candidate exopolysaccharide. The expression of matrix proteins in fibroblasts from the 39 year old donor and the 54 year old donor are analyzed by quantitative PCR.

Human Epidermal Keratinocytes, (HEK) cells (Cell Applications) from a 39 year old donor and a 54 year-old donor are grown in 75-cm$^2$ flasks at a density of 3-5×10$^3$ cells/cm$^2$ in Epilife® supplemented with EDGS (Gibco) and Human Dermal Fibroblast (HDF) cells (Cell Applications) from the 39 year old donor and the 54 year-old donor are grown in 75-cm$^2$ flasks at a density of 7-8×10$^3$ cells/cm$^2$ in 106 medium supplemented with LSGS at 37° C. in 5% CO$_2$ humidified air during 7 days. After this time, the HEK are split and then seeded for treatment. HEK cells from the 39 year old and the 54 year old donors are seeded at a density of 6×10$^5$ cells/well in 6-well plates. After 24 hours incubation at 37° C. in 5% CO$_2$ humidified air, the medium is removed. HEK cells from the 54 year old donor are incubated with 0.02 mg/ml of the exopolysaccharide produced by the strain of *Halomonas eurihalina* species with deposit number LMG P-28571 obtained in accordance with example 1 in fresh culture medium. As a basal control, three wells of HEK cells from the 54 year old donor are incubated with medium only. As a basal positive, three wells of HEK cells from the 39 year old donor are incubated with medium only. Incubation conditions are 37° C. and 5% CO$_2$ for 24 h. All treatments are made in three wells per set of culture conditions. HDF cells are seeded at a density of 1.7-2.4×10$^6$ cells/well in 25-cm$^2$ flasks. After 24 hours incubation at 37° C. in 5% CO$_2$ humidified air, medium is removed and the HDF cells incubated with the supernatants of the keratinocytes cultures.

24 h after incubation, HDF are lysed directly in the wells following the protocol described on the RNeasy Mini kit (Qiagen) according to the manufacture's protocol. The lysed cells are homogenized and the RNases are inactivated. The genomic DNA is removed from the samples by using gDNA Eliminator spin columns. Then, the samples are passed through special RNA binding columns and, after several microcentrifugation washes to eliminate contaminants and impurities, the purified RNA is eluted with 50 μl of ultrapure water. Quantification and analysis of purity of RNA samples are performed after RNA elution with a biophotometer (Eppendorf). 3 μg of high quality RNA are retrotranscribed with iScript advanced (BioRad, Hercules, Calif., USA) in a final volume of 20 µl. Complete reaction mix is incubated in a thermal cycler (Eppendorf) at 42° C. for 30 minutes, the reaction is stopped at 85° C. for 5 minutes. Complementary DNA is amplified by qPCR in a real-time PCR thermocycler (BioRad) using SYBR® green supermix (BioRad) in the Extracellular Matrix customized 96-well panel for use with SYBR® Green (BioRad). SYBR® Green binds to double-stranded DNA molecules and emits fluorescence which is quantified and is proportional to the amount of the product in the PCR reaction. Cycling conditions in BioRad CFX96 instrument are 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression ($\Delta\Delta(Ct)$) method with default threshold values using CFX Manager Software (BioRad).

The results obtained respect to the 54 year old donor HDF basal control (100%), are shown in Table 7. The value represents the mean of 5 independent experiments.

TABLE 7

| Symbol | Gene Name | 39 year old donor HDF Relative Levels (%) | 54 year old donor HDF treated with supernatant from 54 year old donor keratinocytes treated with exopolysaccharide Relative Levels (%) |
|---|---|---|---|
| COL3A1 | Collagen, Type III, Alpha 1 | 284.5 | 123.7 |
| ITGA1 | Integrin, Alpha 1 | 217.6 | 133.8 |
| VCAM1 | Vascular Cell Adhesion Molecule 1 | 1908.5 | 185.6 |
| ADAMTS1 | Metallopeptidase With Thrombospondin Type 1 Motif, 1 | 76.4 | 77.6 |
| HYAL1 | Hyaluronoglucosaminidase | 40.1 | 41.3 |
| MMP9 | Matrix Metallopeptidase 9 | 26.1 | 69.2 |

The results show that the exopolysaccharide of the invention upregulates genes involved in the synthesis of the extracellular matrix and downregulates genes involved in the degradation of the extracellular matrix in fibroblasts from the older donor.

Example 6: Induction of Connexin Protein Expression Levels on Reconstructed Human Epidermis by Treatment with the Exopolysaccharide Produced by the Strain of *Halomonas eurihalina* Species with Deposit Number LMG P-28571, Using an Immunohistochemistry Assay Gap Junctions (GJs) are channels formed by integral membrane proteins called connexins (Cxs). In the epidermal compartment, one aging-induced alteration related to GJs is Cxs down-regulation. To study the expression of connexin proteins, Cx37, Cx30.3, Cx30 and Cx59, in human keratinocytes, we use a three-dimensional culture system, reconstructed human epidermal tissue (RHE), that reproduces in vitro the histological organization of human epidermis in situ.

The SkinEthic™ human tissue models (EPISKIN™) are removed from the agarose-nutrient solution in the multiwell plate immediately after arrival and are placed in a 6-well plate in which each well has previously been filled with SkinEthic Growth Medium (EPISKIN). After overnight incubation at 37° C., 5% $CO_2$, RHE is treated with 0.02 mg/ml of the exopolysaccharide produced by the strain of *Halomonas eurihalina* species with deposit number LMG P-28571 obtained in accordance with example 1, and with medium only (basal conditions), for 24 hours at 37° C. and 5% $CO_2$. After 24 hours of treatment, the tissue models are fixed in 4% paraformaldehyde (Sigma) for 3 hours at 4° C. and are washed 4 times with phosphate-buffered saline (PBS) (Sigma). Then, samples are treated to a sucrose gradient from 0.6M to 2.3M with incubations of 3 hours at room temperature. After the last incubation, the tissue models are embedded in Tissue Tek® OCT compound (Aname). Frozen tissue sections of about 10 µm thickness are cut using a cryomicrotome (Leica, CM3050), collected on coated slides and finally stored at −20° C.

The expression of specific connexins is evaluated by immunohistochemistry with specific primary antibodies and a fluorescently labelled secondary antibody. Defrosted slides are fixed with frozen solution of acetone for 10 min at room temperature then are rinsed with PBS. Non-specific sites are saturated with 10% normal goat serum for 30 minutes at room temperature. After rinsing with 0.2% Tween in PBS, the slides are incubated with the primary antibodies (Anti-Connexin 37/GJA4, 30.3/GJB4, 59/GJA10 antibody (Abcam), Rabbit anti-Connexin 30 (Invitrogen) (diluted in 10% goat serum in PBS) in a humidified chamber at room temperature for 2 hours. At the end of the incubation, slides are washed with 0.2% Tween in PBS and are incubated with Alexa Fluor® 488 Goat anti-rabbit IgG (H+L) secondary antibody (Invitrogen, green fluorescence emission dye) for 1 hour at room temperature in a dark humidified chamber. After rinsing with PBS, the sections are mounted in prolong Gold antifade reagent with Dapi (Invitrogen).

Microscopical observations are performed with a Zeiss fluorescence microscopy and photographs of each condition are taken with the associated camera. From each fluorescence image of connexins, values of ID (Integrated Density) are quantified and normalized by control. At least 4 representative images from each condition are collected and analyzed with the Imagen J software. The mean represents the data of 1 or 2 independent experiments.

The results obtained respect to basal conditions (100%) are shown in Table 8.

TABLE 8

| Connexin protein | Protein Levels (%) |
|---|---|
| Cx59 protein | 127.8 |
| Cx37 protein | 205.1 |
| Cx30 protein | 152.3 |
| Cx30.3 protein | 156.5 |

The results show that the exopolysaccharide of the invention induces a significant increase in the expression of connexin proteins in keratinocytes from reconstructed human epidermis at the tested concentration.

Example 7: Restoring the Levels of Connexin Expression in an In Vitro Menopause Model by Treatment with the Exopolysaccharide Produced by the Strain of *Halomonas eurihalina* Species with Deposit Number LMG P-28571

Skin aging is produced by extrinsic as well as intrinsic factors, among them a decline in endocrine gland function and a reduction in the levels of circulating hormones. The menopause causes hypoestrogenism, accelerating age-related deterioration of the skin. Following the menopause, many women detect a swift commencement of skin aging; skin becomes thinner with decreased collagen content, decreased elasticity, increased wrinkling and increased dryness. In postmenopausal women skin thickness decreases by 1.13% per postmenopausal year, with an associated decrease in collagen content (2% per post-menopausal year). Gap-junctional intercellular communication (GJIC) is considered to play an important role in the control of cell growth, differentiation, the maintenance of homeostasis and morphogenesis. GJIC is regulated by various factors, including growth factors, oncogenes, Ca2+, pH and hormones. Hormones are involved in the regulation of intracellular communication via GJIC. The aim of this study is to investigate the relationship between the decrease of gap junctional intercellular communication and hormonal skin aging. Thus, we developed an in vitro model of menopause in keratinocytes by treating them with hormone levels of menopausal women. Keratinocytes treated with hormone levels of non-menopausal women were used as a basal control. In this study, the efficacy of the exopolysaccharide produced by the strain of *Halomonas eurihalina* species with deposit number LMG P-28571, obtained in accordance with example 1, at restoring the levels of connexins in menopausal keratinocytes is evaluated by RT-qPCR array system.

Human Epidermal Keratinocytes HEK cells (Cell Applications), from a 19 year old donor are grown in 75-cm$^2$ flasks at a density of 3-5×10$^3$ cells/cm$^2$ in Epilife® supplemented with 10% EDGS (Gibco) at 37° C. in 5% $CO_2$ humidified air for 7 days. After this time, they are split and then seeded for treatment. HEK cells are seeded at a density of 6-7.5×10$^5$ cells/well in 6-well plates in Epilife supplemented with 0.1% EDGS. After 24 hours incubation at 37° C. in 5% $CO_2$ humidified air, the medium is removed. Then, to stimulate menopause conditions, keratinocytes are incubated with menopausal hormones concentrations and with 0.02 mg/ml of the exopolysaccharide produced by the strain of *Halomonas eurihalina* species with deposit number LMG P-28571 obtained in accordance with example 1, and with medium only with menopausal hormone concentrations. Two wells of these cells are incubated with non-menopausal hormones concentrations as a basal control. The incubation conditions are 37° C. and 5% $CO_2$ for 24 h. All treatments are made in two wells per set of culture conditions.

Concentrations of hormones in conditions of non-menopausal and menopausal are shown in Table 9.

TABLE 9

| Hormone | Concentration in Non-menopausal conditions | Concentration in Menopausal conditions |
|---|---|---|
| β-Estradiol | 750 pM | 60 pM |
| Progesterone | 60 nM | 6 nM |
| Dehydroepiendrosterone | 20 nM | 2 nM |
| Human Growth hormone | 0.005 µg/ml | 0.0015 µg/ml |
| Insuline-like growth factor-1 | 0.2 µg/ml | 0.1 µg/ml |

24 h after incubation, the cells are lysed directly in the wells following the protocol described on the RNeasy™ Mini kit (Qiagen) according to the manufacture's protocol. The lysed cells are homogenized and the RNases are inactivated. The genomic DNA is removed from the samples by using gDNA Eliminator spin columns. Then, the samples are passed through special RNA binding columns and, after several microcentrifugation washes to eliminate contaminants and impurities, the purified RNA is eluted with 50 µl of ultrapure water. Quantification and analysis of purity of RNA samples are performed after RNA elution with a biophotometer (Eppendorf). 3 µg of high quality RNA are retrotranscribed with iScript advanced (BioRad) in a final volume of 20 µl. Complete reaction mix is incubated in a thermal cycler (Eppendorf) at 42° C. for 30 minutes, the reaction is stopped at 85° C. for 5 min. Complementary DNA is amplified by qPCR in a real-time PCR thermocycler (BioRad) using SYBR®green supermix (BioRad) in the Human Gap junctions Predesigned 96-well panel for use with SYBR® Green (BioRad). SYBR Green binds to double-stranded DNA molecules and emits fluorescence which is quantified and is proportional to the amount of the product in the PCR reaction. Cycling conditions in BioRad CFX96 instrument are 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression ($\Delta\Delta(Ct)$) method with default threshold values using CFX Manager Software (BioRad).

The results obtained respect to the non-menopausal conditions HEK cells (100%) are shown in Table 10. The value represents the mean of 5 independent experiments.

TABLE 10

| Symbol | Gene Name | Menopausal HEK Relative Levels (%) | Menopausal HEK treated with exopolysaccharide Relative Levels (%) |
|---|---|---|---|
| GJA3 | Gap junction alpha-3 protein | 74.48 | 262.69 |
| GJA4 | Gap junction alpha-3 protein | 71.99 | 173.31 |
| GJA9 | Gap junction alpha-9 protein | 76.02 | 247.65 |
| GJB3 | Gap junction beta-3 protein | 83.22 | 130.25 |
| GJB4 | Gap junction beta-4 protein | 89.31 | 212.99 |

The results show that the exopolysaccharide of the invention restores the levels of connexins in menopausal keratinocytes.

Example 8: Restoring the Levels of Connexin Expression in Older Keratinocytes with Treatment of Exopolysaccharide Produced by the Strain of *Halomonas eurihalina* Species with Deposit Number LMG P-28571

Aging is a result of damage that has accumulated within the skin which has lost the part of its communication network. In the epidermal compartment, one aging-induced alteration relates to gap junctions, i.e. transmembrane channels between two neighboring cells, enabling ion exchange. Indeed, expression of their components, the connexins (Cx), is down-regulated during aging. Thus, the aim of this study is to investigate the antiaging efficacy of the exopolysaccharide produced by the strain of *Halomonas eurihalina* species with deposit number LMG P-28571 by evaluating connexin expression in older keratinocytes compared to younger keratinocytes by RT-qPCR array system.

Human Epidermal Keratinocytes, HEK cells (Cell Applications), are grown in 75-cm$^2$ flasks at a density of 2-4×10$^5$ cells/flask in Epilife supplemented with EDGS (Gibco) at 37° C. in 5% $CO_2$ humidified air for 7 days. After this time, they are split and then seeded for treatment. HEK cells from the 39 year old donor and the 54 year old donor are seeded at a density of 6×10$^5$ cells/well in 6-well plates in the culture medium. After 24 hours incubation at 37° C. in 5% $CO_2$ humidified air, the medium is removed. The keratinocytes from the 54 year old donor are incubated with 0.02 mg/ml of the exopolysaccharide produced by the strain of *Halomonas eurihalina* species with deposit number LMG P-28571 obtained in accordance with example 1 in fresh culture medium. Two wells of these cells are incubated with fresh medium as a basal control. As a positive control, two wells of keratinocytes from a 39 year old donor are incubated with fresh medium. The incubation conditions are 37° C. and 5% $CO_2$ for 24 hours. All treatments are made in two wells per set of culture conditions.

24 hours after incubation, the cells are lysed directly in the wells following the protocol described on the RNeasy Mini kit (Qiagen) according to the manufacture's protocol. The lysed cells are homogenized and the RNases are inactivated. The genomic DNA is removed from the samples by using gDNA Eliminator spin columns. Then, the samples are passed through special RNA binding columns and after several microcentrifugation washes to eliminate contaminants and impurities, the purified RNA is eluted with 50 μl of ultrapure water. Quantification and analysis of purity of RNA samples are performed after RNA elution with a biophotometer (Eppendorf). 3 μg of high quality RNA are retrotranscribed with iScript advanced (BioRad) in a final volume of 20 μl. Complete reaction mix is incubated in a thermal cycler (Eppendorf) at 42° C. for 30 minutes, the reaction is stopped at 85° C. for 5 minutes. Complementary DNA is amplified by qPCR in a real-time PCR thermocycler (BioRad) using SYBRgreen supermix (BioRad) in the Human Gap junctions Predesigned 96-well panel for use with SYBR® Green (BioRad). SYBR Green binds to double-stranded DNA molecules and emits fluorescence which is quantified and is proportional to the amount of the product in the PCR reaction. Cycling conditions in BioRad CFX96 instrument are 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes is calculated using normalized expression (ΔΔ(Ct)) method with default threshold values using CFX Manager Software (BioRad).

The results obtained respect to the 54 year old donor HEK basal control (100%) are shown in Table 11. The value represents the mean of 4 independent experiments.

TABLE 11

| Symbol | Gene Name | 39 year old donor HEK Relative Levels (%) | 54 year old donor HEK treated with the exopolysaccharide Relative Levels (%) |
| --- | --- | --- | --- |
| GJA1 | Gap junction alpha-1 protein | 149.2 | 162.16 |
| GJA9 | Gap junction alpha-9 protein | 128.3 | 189.6 |
| GJB2 | Gap junction beta-2 protein | 142.6 | 183.2 |
| GJB6 | Gap junction beta-6 protein | 211.8 | 194.9 |

The results show that the exopolysaccharide of the invention restores the connexin expression in keratinocytes from a 54 year old donor to that found in younger skin cells.

Example 9: Restoring the Levels of Connexin Protein Expression in an In Vitro Model of Menopause in Reconstructed Human Epidermal Tissue by Treatment with the Exopolysaccharide Produced by the Strain of *Halomonas eurihalina* Species with Deposit Number LMG P-28571, Using an Immunohistochemistry Assay Skin aging is produced by extrinsic as well as intrinsic factors, among them a decline in endocrine gland function and a reduction in the levels of circulating hormones. The menopause causes hypoestrogenism, accelerating age-related deterioration of the skin. Following menopause many women detect a swift commencement of skin aging; skin becomes thinner with decreased collagen content, decreased elasticity, increased wrinkling and increased dryness. In postmenopausal women skin thickness decreases by 1.13% per postmenopausal year, with an associated decrease in collagen content (2% per post-menopausal year). Gap-junctional intercellular communication (GJIC) is considered to play an important role in the control of cell growth, differentiation, the maintenance of homeostasis and morphogenesis. GJIC is regulated by various factors, including growth factors, oncogenes, Ca2+, pH and hormones. Hormones are involved in the regulation of intracellular communication via GJIC. The aim of this study was to investigate the relationship between the decrease of gap junctional intercellular communication and hormonal skin aging. We developed an in vitro model of menopause in reconstructed human epidermal tissue (RHE) treated with hormone levels of menopausal women. As a comparison, reconstructed human epidermal tissue (RHE) treated with hormone levels of non-menopausal women is used. In this study, the efficacy of the exopolysaccharide produced by the strain of *Halomonas eurihalina* species with deposit number LMG P-28571 obtained in accordance with example 1 at restoring the levels of connexin proteins, Cx59 and Cx37, by immunohistochemistry.

The SkinEthic human tissue models (EPISKIN) are removed from the agarose-nutrient solution in the multiwell plate immediately after arrival and are placed in a 6-well plate in which each well has previously be filled with SkinEthic Growth Medium (EPISKIN). After overnight incubation at 37° C., 5% $CO_2$, the medium is removed. Then, to stimulate menopause conditions, RHE is incubated with menopausal hormones concentrations and with 0.02 mg/ml of the exopolysaccharide produced by the strain of *Halomonas eurihalina* species with deposit number LMG P-28571 obtained in accordance with example 1, and with medium only with menopausal hormones concentrations. RHE is incubated with non-menopausal hormones concentrations as a positive control. Incubation conditions are 37° C. and 5% $CO_2$ for 24 hours. The RHE samples are embedded in Tissue Teck OCT compound (Aname). All treatments are made in two RHE samples per set of culture conditions.

Concentrations of hormones in for non-menopausal and menopausal conditions are shown in Table 12.

TABLE 12

| Hormone | Concentration in Non-menopausal conditions | Concentration in Menopausal conditions |
| --- | --- | --- |
| β-Estradiol | 750 pM | 60 pM |
| Progesterone | 60 nM | 6 nM |
| Dehydroepiendrosterone | 20 nM | 2 nM |
| Human Growth hormone | 0.005 µg/ml | 0.0015 µg/ml |
| Insuline-like growth factor-1 | 0.2 µg/ml | 0.1 µg/ml |

After 24 hours of treatment, the tissue models are fixed in 4% paraformaldehyde (Sigma) for 3 hours at 4° C. and are washed 4 times with phosphate-buffered saline (PBS) (Sigma). Then, samples are treated to a sucrose gradient from 0.6M to 2.3M with incubations of 3 hours at room temperature. After the last incubation, the tissue models are embedded in Tissue Teck OCT compound. Frozen tissue sections of about 10 µm thickness are cut using a cryomicrotome (Leica, CM3050), collected on coated slides and finally stored at −20° C.

The expression of specific connexins is evaluated by immunohistochemistry with specific primary antibodies and a fluorescently labelled secondary antibody. Defrosted slides are fixed with frozen solution of acetone for 10 minutes at room temperature then are rinsed with PBS. Non-specific sites are saturated with 10% normal goat serum for 30 min at room temperature. After rinsing with 0.2% Tween in PBS, the slides are incubated with the primary antibodies (Anti-Connexin 37/GJA4 and 59/GJA10 antibody (Abcam), diluted in 10% goat serum in PBS) in a humidified chamber at room temperature for 2 hours. At the end of the incubation, slides are washed with 0.2% Tween in PBS and are incubated with Alexa Fluor® 488 Goat anti-rabbit IgG (H+L) secondary antibody (Invitrogen, green fluorescence emission dye) 1 hour at room temperature in a dark humidified chamber. After rinsing with PBS, the sections are mounted in prolong Gold antifade reagent with Dapi (Invitrogen).

Microscopical observations are performed with a Zeiss fluorescence microscopy and photographs of each condition are taken with the associated camera. From each fluorescence image of connexins, values of ID (Integrated Density is the product of Area and Mean gray value) are quantified and normalized by control. At least 12 representative images from each condition are collected and analyzed with the ZEN software (Zeiss). The value represents the mean of 3 independent experiments.

The results obtained respect to the basal control RHE under menopausal conditions (100%) are shown in Table 13.

TABLE 13

| Connexin protein | Non-Menopausal RHE Protein Levels (%) | Menopausal RHE treated with exopolysaccharide Protein Levels (%) |
| --- | --- | --- |
| Cx59 protein | 135.4 | 144.0 |
| Cx37 protein | 156.1 | 167.2 |

The results show that the exopolysaccharide of the invention restores the levels of connexins in the menopausal RHE to non-menopausal conditions.

Example 10: Effect of the Exopolysaccharide Produced by the Strain of *Halomonas eurihalina* Species with Deposit Number LMG P-28571 on Epidermal-Dermal Cell-Cell Communication in Menopausal Model Aging depletes the communication process between cells. Crosstalk between fibroblasts and keratinocytes is essential for regeneration, repair and growth of the skin, and involves the activity of a number of messengers such as growth factors and cytokines. Keratinocytes are the primary source of growth factors, which may stimulate not only keratinocytes themselves but also fibroblasts through paracrine signaling and greatly affect the molecular constitution of the extracellular matrix (ECM) (Werner S, Krieg T, Smola H. *Keratinocyte-fibroblast interactions in wound healing. J Invest Dermatol.* 2007 May; 127(5):998-1008). In this study, first we aim to show that hormonal decline could reduce paracrine communication between keratinocytes and fibroblasts affecting the synthesis of the extracellular matrix. The effect of the exopolysaccharide produced by the strain of *Halomonas eurihalina* species with deposit number LMG P-28571 obtained in accordance with example 1 between menopausal keratinocyte-fibroblast communication is evaluated and compared with non-menopausal keratinocyte-fibroblast communication. The expression of matrix proteins in fibroblasts treated with supernatant from menopausal keratinocytes and with supernatant from non-menopausal keratinocytes is analyzed by quantitative PCR.

Human Epidermal Keratinocytes (HEKa) cells (Cell Applications) from a 19 year old donor are grown in 75-cm² flasks at a density of 5×10³ cells/cm² in Epilife supplemented with EDGS (Gibco) and Human Dermal Fibroblast from adult (HDFa) cells from an 18 year old donor are grown in 75-cm² flasks at a density of 7-8×10³ cells/cm² in 106 medium supplemented with LSGS (GIBCO) at 37° C. in 5% $CO_2$ humidified air during 7 days. After this time, the HEKa are split and then seeded for treatment. HEKa cells are seeded at a density of 8.5×10⁵ cells/well in 6-well plates in Epilife supplemented with 0.1% EDGS. After 24 hours incubation at 37° C. in 5% $CO_2$ humidified air, the medium is removed. Then, to stimulate menopause conditions, keratinocytes are incubated with menopausal hormones and with 0.02 mg/ml of the exopolysaccharide produced by the strain of *Halomonas eurihalina* species with deposit number LMG P-28571 obtained in accordance with example 1, and with medium only with menopausal hormones as a basal control. Three wells of these cells are incubated with non-menopausal hormones as a positive control. Incubation conditions are at 37° C. and 5% $CO_2$ for 24 h. All treatments are made in three wells per set of culture conditions. HDFa cells are seeded at a density of 1.5×10⁶ cells/well in 25-cm² flasks. After 24 hours incubation at 37° C. in 5% $CO_2$ humidified air, the medium is removed and the HDFa cells are incubated with the supernatant from the keratinocyte cultures.

Concentrations of hormones for non-menopausal and menopausal conditions are shown in Table 14.

TABLE 14

| Hormones | Concentration for Non-menopausal conditions | Concentration for Menopausal conditions |
| --- | --- | --- |
| β-Estradiol | 750 pM | 60 pM |
| Progesterone | 60 nM | 6 nM |
| Dehydroepiendrosterone | 20 nM | 2 nM |
| Human Growth hormone | 0.005 µg/ml | 0.0015 µg/ml |
| Insuline-like growth factor-1 | 0.2 µg/ml | 0.1 µg/ml |

24 hours after incubation, HDFa are lysed directly in the wells following the protocol described on the RNeasy Mini kit (Qiagen) according to the manufacture's protocol. The lysed cells are homogenized and the RNases are inactivated. The genomic DNA is removed from the samples by using gDNA Eliminator spin columns. Then, the samples are passed through special RNA binding columns and after several microcentrifugation washes to eliminate contaminants and impurities, the purified RNA is eluted with 50 µl of ultrapure water. Quantification and analysis of purity of RNA samples were performed after RNA elution with a biophotometer. 1 µg of high quality RNA were retrotranscribed with iScript advanced (BioRad) in a final volume of 20 µl. Complete reaction mix is incubated in a thermal cycler (Eppendorf) at 42° C. for 30 minutes, the reaction is stopped at 85° C. for 5 minutes. Complementary DNA is amplified by qPCR in a real-time PCR thermocycler (BioRad) using SYBRgreen supermix (BioRad) in the Extracellular Matrix customized 96-well panel for use with SYBR® Green (BioRad). SYBR Green binds to double-stranded DNA molecules and emits fluorescence which is quantified and is proportional to the amount of the product in the PCR reaction. Cycling conditions in BioRad CFX96 instrument are 95° C. for 3 minutes, followed by 40 cycles of denaturing at 95° C. for 5 seconds, annealing and elongation at 60° C. for 30 seconds. GAPDH (Glyceraldehyde 3-phosphate dehydrogenase), TBP (TATA box binding protein) and HRPT1 (hypoxanthine phosphoribosyltransferase 1) are used as endogenous controls. Fold change relative to the expression of the sample genes and reference genes was calculated using normalized expression (ΔΔ(Ct)) method with default threshold values using CFX Manager Software (BioRad).

The results obtained respect to the basal control of HDFa treated with the supernatant from menopausal keratinocytes (100%) are shown in Table 15. The value represents the data of one experiment.

TABLE 15

| Symbol | Gene Name | HDFa treated with supernatant from non-menopausal keratinocytes Relative Levels (%) | HDFa treated with supernatant from menopausal keratinocytes treated with exopolysaccharide Relative Levels (%) |
| --- | --- | --- | --- |
| ACTN1 | actinin, alpha 1 | 126.5 | 137.3 |
| COL11A1 | collagen, type XI, alpha 1 | 130.2 | 122.6 |
| COL12A1 | collagen, type XII, alpha 1 | 126.1 | 123.7 |
| COL16A1 | collagen, type XVI, alpha 1 | 146.0 | 148.2 |
| COL6A2 | collagen, type VI, alpha 2 | 127.3 | 127.6 |
| COL7A1 | collagen, type VII, alpha 1 | 192.6 | 149.4 |
| HAS1 | hyaluronan synthase 1 | 197.6 | 156.9 |
| ICAM1 | intercellular adhesion molecule 1 | 123.7 | 200.0 |
| ITGA5 | integrin, alpha 5 | 132.8 | 132.5 |
| ITGA7 | integrin, alpha 7 | 141.4 | 122.9 |
| ITGA8 | integrin, alpha 8 | 119.1 | 175.4 |
| ITGAV | integrin, alpha V | 121.6 | 134.1 |
| ITGB5 | integrin, beta 5 | 120.2 | 136.6 |
| LAMB3 | laminin, beta 3 | 152.6 | 196.9 |
| LAMC1 | laminin, gamma 1 | 138.6 | 121.2 |
| TGFBI | transforming growth factor, beta-induced, 68 kDa | 137.4 | 126.6 |
| THBS3 | thrombospondin 3 | 216.6 | 117.9 |
| TLN1 | talin 1 | 136.2 | 135.7 |
| VCAN | versican | 121.6 | 117.9 |
| VTN | vitronectin | 499.8 | 242.3 |
| MMP13 | Matrix metallopeptidase 13 | 41.1 | 29.1 |

The results show that the exopolysaccharide of the invention upregulates genes involved in the synthesis of the extracellular matrix and downregulates gene involved in the degradation of the extracellular matrix (MMP13) in fibroblasts treated with supernatant from menopausal keratinocytes.

Example 11: Study of the Increase of the Accumulation of Lipids in Primary Human Subcutaneous Preadipocytes Produced by the Strain of *Halomonas eurihalina* Species with Deposit Number LMG P-28571

One age-related skin alteration is a reduction in subcutaneous fat. Gap Junction Intercellular Communication (GJIC) would seem to play an important role in the adipogenesis process, the process by which preadipocytes become adipocytes in the fat mass.

Quantification of adipogenesis is evaluated with AdipoRed™ Adipogenesis Assay Reagent (Lonza). The increase of the accumulation of lipids is determined by measuring the fluorescence signal of Nile Red in primary human Primary Human Subcutaneous Preadipocytes after treatment with exopolysaccharide produced by the strain of *Halomonas eurihalina* species with deposit number LMG P-28571 obtained in accordance with example 1 in Adipocyte Differentiation Medium. Cells treated with Adipocyte Differentiation Medium alone are used as a basal control.

Human preadipocytes (from a 22 year old donor) (ZEN-BIO) are seeded (13,000 cells/well, 5 wells per condition) in 96-clear well plates in Preadipocyte Growth Medium (ZEN-BIO). The cells are incubated for 24 hours at 37° C. in a water-saturated atmosphere of 95% air and 5% $CO_2$. After incubation, the medium is removed and the cells are incubated with exopolysaccharide produced by the strain of *Halomonas eurihalina* species with deposit number LMG P-28571 obtained in accordance with example 1 at 0.02 mg/ml in Adipocyte Differentiation Medium (ZENBIO) (in order to induce differentiation of preadipocytes into adipocytes) for 8 days at 37° C. and 5% $CO_2$. In the basal control, preadipocytes are treated with the Adipocyte Differentiation Medium only. As a negative control, preadipocytes are treated with the Adipocyte Differentiation Medium and caffeine.

Quantification of the accumulation of lipids is carried out by AdipoRed™ reagent (LONZA) assay. Following the manufacturer's instructions, the differentiated preadipocytes cells for each condition are washed with Phosphate Buffered Saline (PBS) with calcium and magnesium (Sigma) and diluted AdipoRed reagent is added. Upon completion of reagent addition, the cells are incubated at room temperature for 15 minutes. Then, fluorescence of neutral lipids is measured using the ClarioStar (S/N 430-01109) reader (BMG) with excitation and emission wavelengths of 485 nm and 530 nm, respectively. The percentage of normalized lipid accumulation compared with the basal control is calculated.

The results obtained, respect to basal conditions (100%), are shown in Table 16. The value represents the mean of 3 independent experiments.

TABLE 16

| Product | Concentration | % Lipid accumulation vs basal control |
| --- | --- | --- |
| exopolysaccharide | 0.02 mg/mL | 117.93 |
| Caffeine 200 µg/mg | 2.5 µg/mL | 87.50 |

The results show that the exopolysaccharide of the invention increases the percentage of intracellular lipid accumulation during the adipogenic process in human subcutaneous preadipocytes cultures.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

The invention claimed is:

1. A method of treatment and/or care of the skin comprising administering a composition comprising a cosmetically or dermopharmaceutically effective quantity of an exopolysaccharide produced by a strain of *Halomonas eurihalina* species or a ferment extract comprising the exopolysaccharide to the skin, the cosmetically or dermopharmaceutically effective quantity of the exopolysaccharide being between 0.000001% by weight and 5% by weight of the composition,
wherein the exopolysaccharide has a composition by weight of 0.5% to 45% of rhamnose, 0.1% to 25% of galactose, 0.5% to 30% of mannose, 50% to 95% for the sum of glucose and D-glucosamine, 0% to 10% of fucose and 0% to 12% of glucuronic acid, with the condition that the sum of the percentages does not exceed 100%, and
wherein the treatment or care:
i) stimulates collagen synthesis,
ii) increases the level of connexins in the skin,
iii) increases mRNA and protein expression of connexins in keratinocytes,
iv) restores connexin levels in menopausal keratinocytes to premenopausal levels, and/or
v) enhances a percentage of intracellular lipid accumulation during an adipogenic process in human subcutaneous preadipocytes.

2. The method according to claim 1, wherein the exopolysaccharide produced by the strain of *Halomonas eurihalina* species has a molecular weight of at least 10 kDa.

3. The method according to claim 1, wherein the strain of *Halomonas eurihalina* species is a strain of *Halomonas eurihalina* species with deposit number LMG P-28571.

4. The method according to claim 1, wherein the retention time of the exopolysaccharide produced by the strain of *Halomonas eurihalina* is between 4 and 8.5 minutes at a HPLC analysis with a chromatographic column for aqueous Size Exclusion Chromatography, with a particle size of 8 µm, a pore size of 50 Å and a length/Internal Diameter of 300 mm×7.5 mm and 0.1 M sodium acetate in water as eluent with a flow rate of 0.8 ml/min.

5. The method according to claim 1, wherein the cosmetic or dermopharmaceutical composition comprises at least one cosmetically acceptable excipient.

6. The method according to claim 1, wherein the ferment extract is:
incorporated into a cosmetic delivery system;
incorporated into a sustained release system; or
adsorbed on a solid organic polymer or solid mineral support.

7. The method according to claim 1, wherein the composition is in a formulation selected from the group consisting of creams, multiple emulsions, solutions, liquid crystals, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils, sprays, and aerosols.

8. The method according to claim 1, wherein the composition is incorporated into a fabric or a medical device.

9. The method according to claim 1, wherein the exopolysaccharide has been chemically modified by phosphorylation, sulfonation, acylation, esterification, formation of metallic complexes of the exopolysaccharide and/or a chemical sulfation greater than 7%.

10. The method according to claim 1, wherein the exopolysaccharide is between 0.0001% by weight and 5% by weight of the composition.

11. The method according to claim 1, wherein the composition further comprises an agent which increases percutaneous absorption selected from the group consisting of dimethyl sulfoxide, dimethylacetamide, dimethylformamide, surfactants, 1-dodecylazacycloheptane-2-one, alcohol, urea, ethoxydiglycol, acetone, propylene glycol, and polyethylene glycol.

12. The method according to claim 1, wherein the composition comprises:
between 0.1% by weight and 20% by weight of an humectant selected from the group consisting of glycerin, propylene glycol, butylene glycol, pentylene glycol, caprylyl glycol, lactic acid, urea, and sodium hyaluronate;
between 0.1% by weight and 20% by weight of an emollient or skin conditioner selected from the group consisting of dimethicone, glyceryl stearate, caprylic/capric triglyceride, cetearyl alcohol, lecithin, $C_{12}$-$C_{15}$ alkyl benzoate, squalane, lanolin, behenyl alcohol, tocopheryl acetate, panthenol, *Butyrospermum parkii* butter, retinyl palmitate, and retinol; and between 0.1% by weight and 20% by weight of a surfactant selected from the group consisting of xanthan gum, sodium laureth sulfate, stearic acid, Polysorbate 20, Polysorbate 80, stearyl alcohol, cetyl alcohol, steareth-2, ceteareth-20, and cocamidopropyl betaine.

* * * * *